US009511554B2

(12) United States Patent
Dave

(10) Patent No.: US 9,511,554 B2
(45) Date of Patent: Dec. 6, 2016

(54) BIOABSORBABLE POLYMER, NON-BIOABSORBABLE METAL COMPOSITE STENTS

(71) Applicant: Cordis Corporation, Bridgewater, NJ (US)

(72) Inventor: Vipul Dave, Hillsborough, NJ (US)

(73) Assignee: CARDINAL HEALTH SWITZERLAND 515 GmbH (CH)

( * ) Notice: Subject to any disclaimer, the term of this patent is extended or adjusted under 35 U.S.C. 154(b) by 137 days.

(21) Appl. No.: 13/747,624

(22) Filed: Jan. 23, 2013

(65) Prior Publication Data

US 2013/0127094 A1    May 23, 2013

Related U.S. Application Data

(63) Continuation of application No. 11/696,250, filed on Apr. 4, 2007, now abandoned.

(51) Int. Cl.
| B29D 23/00 | (2006.01) |
| A61F 2/91 | (2013.01) |
| A61F 2/915 | (2013.01) |
| A61L 27/44 | (2006.01) |
| A61L 27/54 | (2006.01) |
| A61L 29/12 | (2006.01) |
| A61L 29/16 | (2006.01) |
| A61L 31/12 | (2006.01) |
| A61L 31/16 | (2006.01) |

(52) U.S. Cl.
CPC ............... *B29D 23/00* (2013.01); *A61F 2/91* (2013.01); *A61F 2/915* (2013.01); *A61L 27/446* (2013.01); *A61L 27/54* (2013.01); *A61L 29/126* (2013.01); *A61L 29/16* (2013.01); *A61L 31/128* (2013.01); *A61L 31/16* (2013.01); *A61F 2002/91541* (2013.01); *A61F 2210/0076* (2013.01); *A61F 2250/0031* (2013.01); *A61F 2250/0067* (2013.01); *A61L 2300/00* (2013.01)

(58) Field of Classification Search
None
See application file for complete search history.

(56) References Cited

U.S. PATENT DOCUMENTS

| 6,494,908 B1 | 12/2002 | Huxel et al. |
| 6,565,599 B1 | 5/2003 | Hong et al. |
| 6,743,463 B2 | 6/2004 | Weber et al. |
| 6,746,478 B2 | 6/2004 | Jayaraman et al. |
| 6,770,089 B1 | 8/2004 | Hong et al. |
| 6,805,705 B2 | 10/2004 | Hong et al. |
| 6,866,805 B2 | 3/2005 | Hong et al. |
| 6,932,930 B2 | 8/2005 | DeSimone et al. |

(Continued)

FOREIGN PATENT DOCUMENTS

| EP | 0747069 B1 | 6/1996 |
| EP | 0747069 | 12/1996 |
| WO | 0141678 A2 | 6/2001 |

OTHER PUBLICATIONS

Canadian Office Action dated Jan. 15, 2015 in corresponding Canadian Patent Application No. 2,626,957.

*Primary Examiner* — Monica Huson

(57) ABSTRACT

Biocompatible materials may be configured into any number of implantable medical devices including intraluminal stents. The biocompatible material may comprise metallic and non-metallic materials in hybrid structures. In one such structure, a device may be fabricated with one or more elements having an inner metallic frame that is not degradable with an outer shell formed from a polymeric material that is biodegradable by extrusion blow molding. Additionally, therapeutic agents may be incorporated into the microstructure or the bulk material.

2 Claims, 9 Drawing Sheets

(56) References Cited

U.S. PATENT DOCUMENTS

| | | | |
|---|---|---|---|
| 6,986,785 B2 * | 1/2006 | O'Shaughnessy | A61F 2/958 606/108 |
| 8,046,897 B2 * | 11/2011 | Wang | A61F 2/958 29/505 |
| 8,221,484 B2 * | 7/2012 | Wesselmann | A61F 2/958 623/1.11 |
| 8,291,570 B2 * | 10/2012 | Eidenschink | A61F 2/95 29/283.5 |
| 2003/0033007 A1 | 2/2003 | Sirhan et al. | |
| 2004/0059409 A1 | 3/2004 | Stenzel | |
| 2004/0106987 A1 | 6/2004 | Palasis et al. | |
| 2004/0127970 A1 | 7/2004 | Saunders et al. | |
| 2004/0186553 A1 | 9/2004 | Yan | |
| 2004/0199242 A1 | 10/2004 | Hong et al. | |
| 2005/0033412 A1 | 2/2005 | Wu et al. | |
| 2005/0113903 A1 | 5/2005 | Rosenthal et al. | |
| 2006/0009836 A1 | 1/2006 | Burgermeister et al. | |
| 2008/0279911 A1 | 11/2008 | Sutermeister et al. | |

* cited by examiner

BIOABSORBABLE POLYMER, NON-BIOABSORBABLE METAL COMPOSITE STENTS

CROSS-REFERENCE TO RELATED APPLICATIONS

This application is a continuation application of U.S. application Ser. No. 11/696,250, filed Apr. 4, 2007.

BACKGROUND OF THE INVENTION

1. Field of the Invention

The present invention relates to implantable medical devices, and more particularly, to implantable medical devices fabricated as composite structures.

2. Discussion of the Related Art

Currently manufactured intravascular stents do not adequately provide sufficient tailoring of the microstructural properties of the material forming the stent to the desired mechanical behavior of the device under clinically relevant in-vivo loading conditions. Any intravascular device should preferably exhibit certain characteristics, including maintaining vessel patency through a chronic outward force that will help to remodel the vessel to its intended luminal diameter, preventing excessive radial recoil upon deployment, exhibiting sufficient fatigue resistance and exhibiting sufficient ductility so as to provide adequate coverage over the full range of intended expansion diameters.

Accordingly, there is a need to develop precursory materials and the associated processes for manufacturing intravascular stents that provide device designers with the opportunity to engineer the device to specific applications.

SUMMARY OF THE INVENTION

The present invention overcomes the limitations of applying conventionally available materials to specific intravascular therapeutic applications as briefly described above.

In accordance with one aspect, the present invention is directed to a substantially tubular intraluminal scaffold. The scaffold comprising a plurality of hoop components configured as the primary radial load bearing elements of the intraluminal scaffold and one or more connector elements interconnecting the plurality of hoop components, wherein at least one of the plurality of hoop components and the one or more connector elements comprises a composite structure formed from a non-bioabsorbable metallic material and a bioabsorbable polymeric material.

The implantable medical devices of the present invention may be specifically configured to optimize the number of discrete equiaxed grains that comprise the wall dimension so as to provide the intended user with a high strength, controlled recoil device as a function of expanded inside diameter.

The biocompatible materials for implantable medical devices of the present invention offer a number of advantages over currently utilized materials. The biocompatible materials of the present invention are magnetic resonance imaging compatible, are less brittle than other metallic materials, have enhanced ductility and toughness, and have increased durability. The biocompatible materials also maintain the desired or beneficial characteristics of currently available metallic materials, including strength and flexibility.

The biocompatible materials for implantable medical devices of the present invention may be utilized for any number of medical applications, including vessel patency devices such as vascular stents, biliary stents, ureter stents, vessel occlusion devices such as atrial septal and ventricular septal occluders, patent foramen ovale occluders and orthopedic devices such as fixation devices.

The biocompatible materials of the present invention are simple and inexpensive to manufacture. The biocompatible materials may be formed into any number of structures or devices. The biocompatible materials may be thermomechanically processed, including cold-working and heat treating, to achieve varying degrees of strength and ductility. The biocompatible materials of the present invention may be age hardened to precipitate one or more secondary phases.

The biocompatible materials of the present invention comprise a unique composition and designed-in properties that enable the fabrication of stents that are able to withstand a broader range of loading conditions than currently available stents. More particularly, the microstructure designed into the biocompatible materials facilitates the design of stents with a wide range of geometries that are adaptable to various loading conditions.

The biocompatible materials of the present invention also include non-metallic materials, including polymeric materials. These non-metallic materials may be designed to exhibit properties substantially similar to the metallic materials described herein, particularly with respect to the microstructure design, including the presence of at least one internal grain boundary or its non-metallic equivalent; namely, spherulitic boundary.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
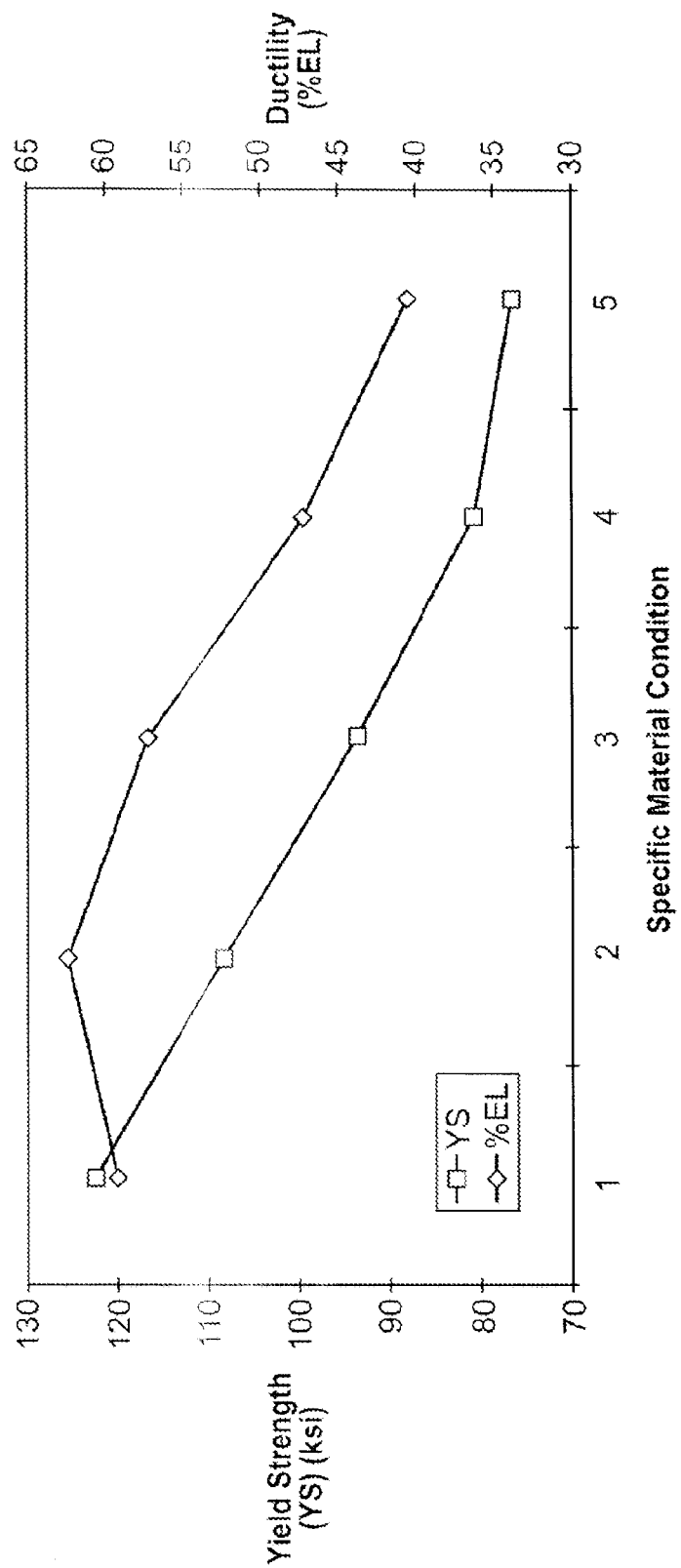
FIG. 1 is a graphical representation of the transition of critical mechanical properties as a function of thermomechanical processing for cobalt-chromium alloys in accordance with the present invention.

Biocompatible, solid-solution strengthened alloys such as iron-based alloys, cobalt-based alloys and titanium-based alloys as well as refractory metals and refractory-based alloys may be utilized in the manufacture of any number of implantable medical devices. The biocompatible alloy for implantable medical devices in accordance with the present invention offers a number of advantages over currently utilized medical grade alloys. The advantages include the ability to engineer the underlying microstructure in order to sufficiently perform as intended by the designer without the limitations of currently utilized materials and manufacturing methodologies.

For reference, a traditional stainless steel alloy such as 316L (i.e. UNS S31603) which is broadly utilized as an implantable, biocompatible device material may comprise chromium (Cr) in the range from about 16 to 18 wt. %, nickel (Ni) in the range from about 10 to 14 wt. %, molybdenum (Mo) in the range from about 2 to 3 wt. %, manganese (Mn) in the range up to 2 wt. %, silicon (Si) in the range up to 1 wt. %, with iron (Fe) comprising the balance (approximately 65 wt. %) of the composition.

Additionally, a traditional cobalt-based alloy such as L605 (i.e. UNS R30605) which is also broadly utilized as an implantable, biocompatible device material may comprise chromium (Cr) in the range from about 19 to 21 wt. %, tungsten (W) in the range from about 14 to 16 wt. %, nickel (Ni) in the range from about 9 to 11 wt. %, iron (Fe) in the range up to 3 wt. %, manganese (Mn) in the range up to 2 wt. %, silicon (Si) in the range up to 1 wt. %, with cobalt (cobalt) comprising the balance (approximately 49 wt. %) of the composition.

Alternately, another traditional cobalt-based alloy such as Haynes 188 (i.e. UNS R30188) which is also broadly utilized as an implantable, biocompatible device material may comprise nickel (Ni) in the range from about 20 to 24 wt. %, chromium (Cr) in the range from about 21 to 23 wt. %, tungsten (W) in the range from about 13 to 15 wt. %, iron (Fe) in the range up to 3 wt. %, manganese (Mn) in the range up to 1.25 wt. %, silicon (Si) in the range from about 0.2 to 0.5 wt. %, lanthanum (La) in the range from about 0.02 to 0.12 wt. %, boron (B) in the range up to 0.015 wt. % with cobalt (Co) comprising the balance (approximately 38 wt. %) of the composition.

In general, elemental additions such as chromium (Cr), nickel (Ni), tungsten (W), manganese (Mn), silicon (Si) and molybdenum (Mo) were added to iron- and/or cobalt-based alloys, where appropriate, to increase or enable desirable performance attributes, including strength, machinability and corrosion resistance within clinically relevant usage conditions.

In accordance with one exemplary embodiment, a cobalt-based alloy may comprise from about nil to about metallurgically insignificant trace levels of elemental iron (Fe) and elemental silicon (Si), elemental iron only, or elemental silicon only. For example, the cobalt-based alloy may comprise chromium in the range from about 10 weight percent to about 30 weight percent, tungsten in the range from about 5 weight percent to about 20 weight percent, nickel in the range from about 5 weight percent to about 20 weight percent, manganese in the range from about 0 weight percent to about 5 weight percent, carbon in the range from about 0 weight percent to about 1 weight percent, Iron in an amount not to exceed 0.12 weight percent, silicon in an amount not to exceed 0.12 weight percent, phosphorus in an amount not to exceed 0.04 weight percent, sulfur in an amount not to exceed 0.03 weight percent and the remainder cobalt. Alternately, the cobalt-based alloy may comprise chromium in the range from about 10 weight percent to about 30 weight percent, tungsten in the range from about 5 weight percent to about 20 weight percent, nickel in the range from about 5 weight percent to about 20 weight percent, manganese in the range from about 0 weight percent to about 5 weight percent, carbon in the range from about 0 weight percent to about 1 weight percent, iron in an amount not to exceed 0.12 weight percent, silicon in an amount not to exceed 0.4 weight percent, phosphorus in an amount not to exceed 0.04 weight percent, sulfur in an amount not to exceed 0.03 weight percent and the remainder cobalt. In yet another alternative composition, the cobalt-based alloy may comprise chromium in the range from about 10 weight percent to about 30 weight percent, tungsten in the range from about 5 weight percent to about 20 weight percent, nickel in the range from about 5 weight percent to about 20 weight percent, manganese in the range from about 0 weight percent to about 5 weight percent, carbon in the range from about 0 weight percent to about 1 weight percent, iron in an amount not to exceed 3 weight percent, silicon in an amount not to exceed 0.12 weight percent, phosphorus in an amount not to exceed 0.04 weight percent, sulfur in an amount not to exceed 0.03 weight percent and the remainder cobalt.

In accordance with another exemplary embodiment, an implantable medical device may be formed from a solid-solution alloy comprising nickel in the range from about 20 weight percent to about 24 weight percent, chromium in the range from about 21 weight percent to about 23 weight percent, tungsten in the range from about 13 weight percent to about 15 weight percent, manganese in the range from about 0 weight percent to about 1.25 weight percent, carbon in the range from about 0.05 weight percent to about 0.15 weight percent, lanthanum in the range from about 0.02 weight percent to about 0.12 weight percent, boron in the range from about 0 weight percent to about 0.015 weight percent, iron in an amount not to exceed 0.12 weight percent, silicon in an amount not to exceed 0.12 weight percent and the remainder cobalt.

In accordance with another exemplary embodiment, an implantable medical device may be formed from a solid-solution alloy comprising nickel in the range from about 20 weight percent to about 24 weight percent, chromium in the range from about 21 weight percent to about 23 weight percent, tungsten in the range from about 13 weight percent to about 15 weight percent, manganese in the range from about 0 weight percent to about 1.25 weight percent, carbon in the range from about 0.05 weight percent to about 0.15 weight percent, lanthanum in the range from about 0.02 weight percent to about 0.12 weight percent, boron in the range from about 0 weight percent to about 0.015 weight percent, silicon in the range from about 0.2 weight percent to about 0.5 weight percent, iron in an amount not to exceed 0.12 weight percent and the remainder cobalt In accordance with yet another exemplary embodiment, an implantable medical device may be formed from a solid-solution alloy comprising nickel in the range from about 20 weight percent to about 24 weight percent, chromium in the range from about 21 weight percent to about 23 weight percent, tungsten in the range from about 13 weight percent to about 15 weight percent, iron in the range from about 0 weight percent to about 3 weight percent, manganese in the range from about 0 weight percent to about 1.25 weight percent, carbon in the range from about 0.05 weight percent to about 0.15 weight percent, lanthanum in the range from about 0.02 weight percent to about 0.12 weight percent, boron in the range from about 0 weight percent to about 0.015 weight percent, silicon in an amount not to exceed 0.12 weight percent and the remainder cobalt.

In contrast to the traditional formulation of this alloy (i.e. Alloy 188/Haynes 188), the intended composition does not include any elemental iron (Fe) or silicon (Si) above conventional accepted trace impurity levels. Accordingly, this exemplary embodiment will exhibit a marked reduction in 'susceptibility' (i.e. the magnetic permeability) thereby leading to improved magnetic resonance imaging compatibility. Additionally, the exemplary embodiment will exhibit a marked improvement in material ductility and fatigue strength (i.e. cyclic endurance limit strength) due to the elimination of silicon (Si), above trace impurity levels.

The composition of the material of the present invention does not eliminate ferromagnetic components but rather shift the 'susceptibility' (i.e. the magnetic permeability) such that the magnetic resonance imaging compatibility may be improved. In addition, the material of the present invention is intended to improve the measurable ductility by minimizing the deleterious effects induced by traditional machining aides such as silicon (Si).

It is important to note that any number of alloys and engineered metals, including iron-based alloys, cobalt-based alloys, refractory-based alloys, refractory metals, and titanium-based alloys may be used in accordance with the present invention. However, for ease of explanation, a detailed description of a cobalt-based alloy will be utilized in the following detailed description.

An exemplary embodiment may be processed from the requisite elementary raw materials, as set-forth above, by first mechanical homogenization (i.e. mixing) and then compaction into a green state (i.e. precursory) form. If necessary, appropriate manufacturing aids such as hydrocarbon based lubricants and/or solvents (e.g. mineral oil, machine oils, kerosene, isopropanol and related alcohols) be used to ensure complete mechanical homogenization. Additionally, other processing steps such as ultrasonic agitation of the mixture followed by cold compaction to remove any unnecessary manufacturing aides and to reduce void space within the green state may be utilized. It is preferable to ensure that any impurities within or upon the processing equipment from prior processing and/or system construction (e.g. mixing vessel material, transfer containers, etc.) be sufficiently reduced in order to ensure that the green state form is not unnecessarily contaminated. This may be accomplished by adequate cleaning of the mixing vessel before adding the constituent elements by use of surfactant-based cleaners to remove any loosely adherent contaminants.

Initial melting of the green state form into an ingot of desired composition, is achieved by vacuum induction melting (VIM) where the initial form is inductively heated to above the melting point of the primary constituent elements within a refractory crucible and then poured into a secondary mold within a vacuum environment (e.g. typically less than or equal to $10^{-4}$ mmHg). The vacuum process ensures that atmospheric contamination is significantly minimized. Upon solidification of the molten pool, the ingot bar is substantially single phase (i.e. compositionally homogenous) with a definable threshold of secondary phase impurities that are typically ceramic (e.g. carbide, oxide or nitride) in nature. These impurities are typically inherited from the precursor elemental raw materials.

A secondary melting process termed vacuum arc reduction (VAR) is utilized to further reduce the concentration of the secondary phase impurities to a conventionally accepted trace impurity level (i.e. <1,500 ppm). Other methods maybe enabled by those skilled in the art of ingot formulation that substantially embodies this practice of ensuring that atmospheric contamination is minimized. In addition, the initial VAR step may be followed by repetitive VAR processing to further homogenize the solid-solution alloy in the ingot form. From the initial ingot configuration, the homogenized alloy will be further reduced in product size and form by various industrially accepted methods such as, but not limited too, ingot peeling, grinding, cutting, forging, forming, hot rolling and/or cold finishing processing steps so as to produce bar stock that may be further reduced into a desired raw material form.

In this exemplary embodiment, the initial raw material product form that is required to initiate the thermomechanical processing that will ultimately yield a desired small diameter, thin-walled tube, appropriate for interventional devices, is a modestly sized round bar (e.g. one inch in diameter round bar stock) of predetermined length. In order to facilitate the reduction of the initial bar stock into a much smaller tubing configuration, an initial clearance hole must be placed into the bar stock that runs the length of the product. These tube hollows (i.e. heavy walled tubes) may be created by 'gun-drilling' (i.e. high depth to diameter ratio drilling) the bar stock. Other industrially relevant methods of creating the tube hollows from round bar stock may be utilized by those skilled-in-the-art of tube making.

Consecutive mechanical cold-finishing operations such as drawing through a compressive outer-diameter (OD), precision shaped (i.e. cut), circumferentially complete, diamond die using any of the following internally supported (i.e. inner diameter, ID) methods, but not necessarily limited to these conventional forming methods, such as hard mandrel (i.e. relatively long traveling ID mandrel also referred to as rod draw), floating-plug (i.e. relatively short ID mandrel that 'floats' within the region of the OD compressive die and fixed-plug (i.e. the ID mandrel is 'fixed' to the drawing apparatus where relatively short work pieces are processed) drawing. These process steps are intended to reduce the outer-diameter (OD) and the corresponding wall thickness of the initial tube hollow to the desired dimensions of the finished product.

When necessary, tube sinking (i.e. OD reduction of the workpiece without inducing substantial tube wall reduction) is accomplished by drawing the workpiece through a compressive die without internal support (i.e. no ID mandrel). Conventionally, tube sinking is typically utilized as a final or near-final mechanical processing step to achieve the desired dimensional attributes of the finished product.

Although not practically significant, if the particular compositional formulation will support a single reduction from the initial raw material configuration to the desired dimensions of the finished product, in process heat-treatments will not be necessary. Where necessary to achieve intended mechanical properties of the finished product, a final heat-treating step is utilized.

Conventionally, all metallic alloys in accordance with the present invention will require incremental dimensional reductions from the initial raw material configuration to reach the desired dimensions of the finished product. This processing constraint is due to the material's ability to support a finite degree of induced mechanical damage per processing step without structural failure (e.g. strain-induced fracture, fissures, extensive void formation, etc.).

In order to compensate for induced mechanical damage (i.e. cold-working) during any of the aforementioned cold-finishing steps, periodic thermal heat-treatments are utilized to stress-relieve, (i.e. minimization of deleterious internal residual stresses that are the result of processes such as cold-working) thereby increasing the workability (i.e. ability to support additional mechanical damage without measurable failure) of the workpiece prior to subsequent reductions. These thermal treatments are typically, but not necessarily limited to, conducted within a relatively inert environment such as an inert gas furnace (e.g. nitrogen, argon, etc.), an oxygen rarified hydrogen furnace, a conventional vacuum furnace and under less common process conditions, atmospheric air. When vacuum furnaces are utilized, the level of vacuum (i.e. subatmospheric pressure), typically measured in units of mmHg or torr (where 1 mmHg is equal to 1 unit torr), shall be sufficient to ensure that excessive and deteriorative high temperature oxidative processes are not functionally operative during heat treatment. This process may usually be achieved under vacuum conditions of $10^{-4}$ mmHg (0.0001 torr) or less (i.e. lower magnitude).

The stress relieving heat treatment temperature is typically held constant between 82 to 86 percent of the conventional melting point (i.e. industrially accepted liquidus temperature, 0.82 to 0.86 homologous temperatures) within an adequately sized isothermal region of the heat-treating apparatus. The workpiece undergoing thermal treatment is held within the isothermal processing region for a finite period of time that is adequate to ensure that the workpiece has reached a state of thermal equilibrium and such that sufficient time has elapsed to ensure that the reaction kinetics (i.e. time dependent material processes) of stress-relieving and/or process annealing, as appropriate, has been adequately completed. The finite amount of time that the workpiece is held within the processing is dependent upon the method of bringing the workpiece into the process chamber and then removing the working upon completion of heat treatment. Typically, this process is accomplished by, but not limited to, use of a conventional conveyor-belt apparatus or other relevant mechanical assist devices. In the case of the former, the conveyor belt speed and appropriate finite dwell-time, as necessary, within the isothermal region is controlled to ensure that sufficient time at temperature is utilized so as to ensure that the process is completed as intended.

When necessary to achieve desired mechanical attributes of the finished product, heat-treatment temperatures and corresponding finite processing times may be intentionally utilized that are not within the typical range of 0.82 to 0.86 homologous temperatures. Various age hardening (i.e. a process that induces a change in properties at moderately elevated temperatures, relative to the conventional melting point, that does not induce a change in overall chemical composition within the metallic alloy being processed) processing steps may be carried out, as necessary, in a manner consistent with those previously described at temperatures substantially below 0.82 to 0.86 homologous temperature. For cobalt-based alloys in accordance with the present invention, these processing temperatures may be varied between and inclusive of approximately 0.29 homologous temperature and the aforementioned stress relieving temperature range. The workpiece undergoing thermal treatment is held within the isothermal processing region for a finite period of time that is adequate to ensure that the workpiece has reached a state of thermal equilibrium and for that sufficient time is elapsed to ensure that the reaction kinetics (i.e. time dependent material processes) of age hardening, as appropriate, is adequately completed prior to removal from the processing equipment.

In some cases for cobalt-based alloys in accordance with the present invention, the formation of secondary-phase ceramic compounds such as carbide, nitride and/or oxides will be induced or promoted by age hardening heat-treating. These secondary-phase compounds are typically, but not limited to, for cobalt-based alloys in accordance with the present invention, carbides which precipitate along thermodynamically favorable regions of the structural crystallographic planes that comprise each grain (i.e. crystallographic entity) that make-up the entire polycrystalline alloy. These secondary-phase carbides can exist along the intergranular boundaries as well as within each granular structure (i.e. intragranular). Under most circumstances for cobalt-based alloys in accordance with the present invention, the principal secondary phase carbides that are stoichiometrically expected to be present are $M_6C$ where M typically is cobalt (cobalt). When present, the intermetallic $M_6C$ phase is typically expected to reside intragranularly along thermodynamically favorable regions of the structural crystallographic planes that comprise each grain within the polycrystalline alloy in accordance with the present invention. Although not practically common, the equivalent material phenomena can exist for a single crystal (i.e. monogranular) alloy.

Additionally, another prominent secondary phase carbide can also be induced or promoted as a result of age hardening heat treatments. This phase, when present, is stoichiometrically expected to be $M_{23}C_6$ where M typically is chromium (Cr) but is also commonly observed to be cobalt (cobalt) especially in cobalt-based alloys. When present, the intermetallic $M_{23}C_6$ phase is typically expected to reside along the intergranular boundaries (i.e. grain boundaries) within a polycrystalline alloy in accordance with the present invention. As previously discussed for the intermetallic $M_6C$ phase, the equivalent presence of the intermetallic $M_{23}C_6$ phase can exist for a single crystal (i.e. monogranular) alloy, albeit not practically common.

In the case of the intergranular $M_{23}C_6$ phase, this secondary phase is conventionally considered most important, when formed in a manner that is structurally and compositionally compatible with the alloy matrix, to strengthening the grain boundaries to such a degree that intrinsic strength of the grain boundaries and the matrix are adequately balanced. By inducing this equilibrium level of material strength at the microstructural level, the overall mechanical properties of the finished tubular product can be further optimized to desirable levels.

In addition to stress relieving and age hardening related heat-treating steps, solutionizing (i.e. sufficiently high temperature and longer processing time to thermodynamically force one of more alloy constituents to enter into solid solution—'singular phase', also referred to as full annealing) of the workpiece may be utilized. For cobalt-based alloys in accordance with the present invention, the typical solutionizing temperature can be varied between and inclusive of approximately 0.88 to 0.90 homologous temperatures. The workpiece undergoing thermal treatment is held within the isothermal processing region for a finite period of time that is adequate to ensure that the workpiece has reached a state of thermal equilibrium and for that sufficient time is elapsed to ensure that the reaction kinetics (i.e. time dependent material processes) of solutionizing, as appropriate, is adequately completed prior to removal from the processing equipment.

The sequential and selectively ordered combination of thermomechanical processing steps that may comprise but not necessarily include mechanical cold-finishing operations, stress relieving, age hardening and solutionizing can induce and enable a broad range of measurable mechanical properties as a result of distinct and determinable microstructural attributes. This material phenomena can be observed in FIG. 1, which shows a chart that exhibits the affect of thermomechanical processing (TMP) such as cold working and in-process heat-treatments on measurable mechanical properties such as yield strength and ductility (presented in units of percent elongation) in accordance with the present invention. In this example, thermomechanical (TMP) groups one (1) through five (5) were subjected to varying combinations of cold-finishing, stress relieving and age hardening and not necessarily in the presented sequential order. In general, the principal isothermal age hardening heat treatment applied to each TMP group varied between about 0.74 to 0.78 homologous temperatures for group (1), about 0.76 to 0.80 homologous temperatures for group (2), about 0.78 to 0.82 homologous temperatures for group (3), about 0.80 to 0.84 homologous temperatures for group (4) and about 0.82 to 0.84 homologous temperatures for group (5). Each workpiece undergoing thermal treatment was held within the isothermal processing region for a finite period of time that was adequate to ensure that the workpiece reached a state of thermal equilibrium and to ensure that sufficient time was elapsed to ensure that the reaction kinetics of age hardening was adequately completed.

Figure 2:
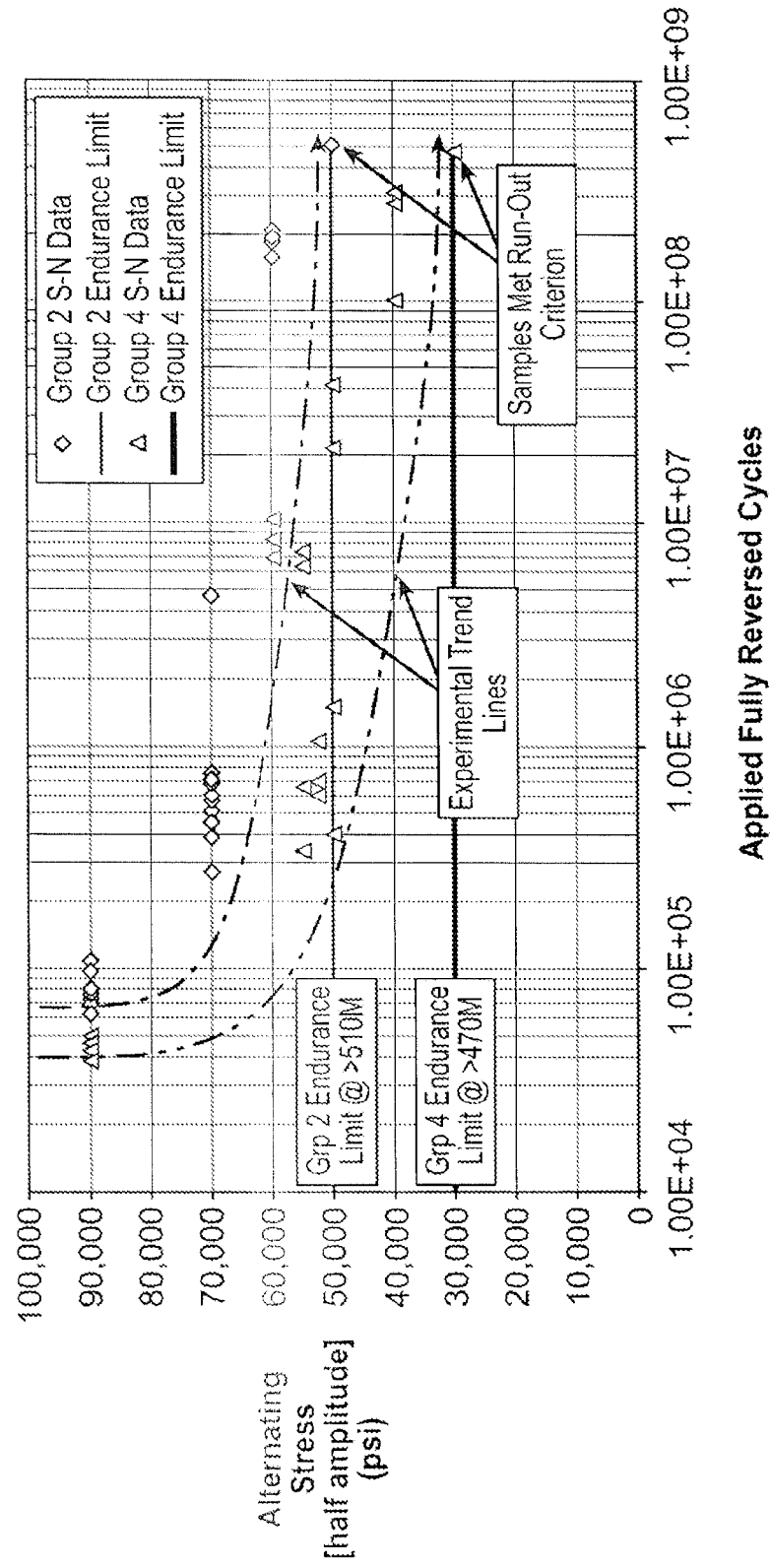
FIG. 2 is a graphical representation of the endurance limit chart as a function of thermomechanical processing for a cobalt-chromium alloy in accordance with the present invention.

More so, the effect of thermomechanical processing (TMP) on cyclic fatigue properties is on cobalt-based alloys, in accordance with the present invention, is reflected in FIG. 2. Examination of FIG. 2, shows the affect on fatigue strength (i.e. endurance limit) as a function of thermomechanical processing for the previously discussed TMP groups (2) and (4). TMP group (2) from this figure as utilized in this specific example shows a marked increase in the fatigue strength (i.e. endurance limit, the maximum stress below which a material can presumably endure an infinite number of stress cycles) over and against the TMP group (4) process.

Other alloys may also be utilized in accordance with the present invention. For reference, a traditional cobalt-based alloy such as MP35N (i.e. UNS R30035) which is also broadly utilized as an implantable, biocompatible device material may comprise a solid-solution alloy comprising nickel in the range from about 33 weight percent to about 37 weight percent, chromium in the range from about 19 weight percent to about 21 weight percent, molybdenum in the range from about 9 weight percent to about 11 weight percent, iron in the range from about 0 weight percent to about 1 weight percent, titanium in the range from about 0 percent to about 1 weight percent, manganese in the range from about 0 weight percent to about 0.15 weight percent, silicon in the range from about 0 weight percent to about 0.15 percent, carbon in the range from about 0 to about 0.025 weigh percent, phosphorous in the range from about 0 to about 0.015 weight percent, boron in the range from about 0 to about 0.015 weight percent, sulfur in the range from about 0 to about 0.010 weight percent, and the remainder cobalt.

As described above, elemental additions such as chromium (Cr), nickel (Ni), manganese (Mn), silicon (Si) and molybdenum (Mo) were added to iron- and/or cobalt-based alloys, where appropriate, to increase or enable desirable performance attributes, including strength, machinability and corrosion resistance within clinically relevant usage conditions.

In accordance with an exemplary embodiment, an implantable medical device may be formed from a solid-solution alloy comprising nickel in the range from about 33 weight percent to about 37 weight percent, chromium in the range from about 19 weight percent to about 21 weight percent, molybdenum in the range from about 9 weight percent to about 11 weight percent, iron in the range from about 0 weight percent to about 1 weight percent, manganese in the range from about 0 weight percent to about 0.15 weight percent, silicon in the range from about 0 weight percent to about 0.15 weight percent, carbon in the range from about 0 weight percent to about 0.015 weight percent, phosphorous in the range from about 0 to about 0.015 weight percent, boron in the range from about 0 to about 0.015 weight percent, sulfur in the range from about 0 to about 0.010 weight percent, titanium in an amount not to exceed 0.015 weight percent and the remainder cobalt.

In contrast to the traditional formulation of MP35N, the intended composition does not include any elemental titanium (Ti) above conventional accepted trace impurity levels. Accordingly, this exemplary embodiment will exhibit a marked improvement in fatigue durability (i.e. cyclic endurance limit strength) due to the minimization of secondary phase precipitates in the form of titanium-carbides.

In accordance with another exemplary embodiment, an implantable medical device may be formed from a biocompatible, solid-solution alloy comprising chromium in the range from about 26 weight percent to about 30 weight percent, molybdenum in the range from about 5 weight percent to about 7 weight percent, nickel in the range from about 0 weight percent to about 1 weight percent, silicon in the range from about 0 weight percent to about 1 weight percent, manganese in the range from about 0 weight percent to about 1 weight percent, iron in the range from about 0 weight percent to about 0.75 weight percent, nitrogen in the range from about 0 to about 0.25 weight percent, carbon in an amount not to exceed 0.025 weight percent and the remainder cobalt.

These alloys may be processed similarly to the other alloys described herein, and exhibit similar characteristics. Once the all intended processing is complete, the tubular product may be configured into any number of implantable medical devices including intravascular stents, filters, occlusionary devices, shunts and embolic coils. In accordance with an exemplary embodiment of the present invention, the tubular product is configured into a stent or intraluminal scaffold. Preferred material characteristics of a stent include strength, fatigue robustness and sufficient ductility.

Strength is an intrinsic mechanical attribute of the raw material. As a result of prior thermomechanical processing, the resultant strength attribute can be assigned primarily to the underlying microstructure that comprises the raw material. The causal relationship between material structure, in this instance, grain size, and the measurable strength, in this instance yield strength, is explained by the classical Hall-Petch relationship where strength is inversely proportional the square of grain size as given by, $$\sigma_y \propto \frac{1}{\sqrt{G.S.}}, \qquad (1)$$

wherein $\sigma_y$ is the yield strength as measured in MPa and G.S. is grain size as measured in millimeters as the average granular diameter. The strength attribute specifically affects the ability of the intravascular device to maintain vessel patency under in-vivo loading conditions.

The causal relationship between balloon-expandable device recoil (i.e. elastic "spring-back" upon initial unloading by deflation of the deployment catheter's balloon) and strength, in this instance yield strength, is principally affected by grain size. As previously described, a decrement in grain-size results in higher yield strength as shown above.

Accordingly, the measurable device recoil is inversely proportional to the grain size of the material.

The causal relationship between fatigue resistance, in this instance endurance limit or the maximum stress below which a material can presumably endure an infinite number of stress cycles, and strength, in this instance yield strength, is principally affected by grain size. Although fatigue resistance is also affected by extrinsic factors such as existing material defects, for example, stable cracks and processing flaws, the principal intrinsic factor affecting fatigue resistance for a given applied load is material strength. As previously described, a decrement in grain-size results in higher yield strength as shown above. Accordingly, the endurance limit (i.e. fatigue resistance) is inversely proportional to the grain size of the material.

The causal relationship between ductility, in this instance the material's ability to support tensile elongation without observable material fracture (i.e. percent elongation), is significantly affected by grain size. Typically, ductility is inversely proportional to strength that would imply a direct relationship to grain size.

In accordance with the exemplary embodiment described herein, microstructural attributes, in this instance, grain-size, may be configured to be equal to or less than about 32 microns in average diameter. In order to ensure that all of the measurable mechanical attributes are homogenous and isotropic within the intended structure or stent, an equiaxed distribution of granularity is preferable. So as to ensure that the structural properties of the intended stent are configured in the preferred manner, a minimum of about two structurally finite intergranular elements (i.e. grains) to a maximum of about ten structurally finite intergranular elements shall exist within a given region of the stent components or elements. In particular, the number of grains may be measured as the distance between the abluminal and the luminal surface of the stent component (i.e. wall thickness). While these microstructural aspects may be tailored throughout the entirety of the stent, it may be particularly advantageous to configure the deformable regions of the stent with these microstructural aspects as described in detail below.

Figure 3:
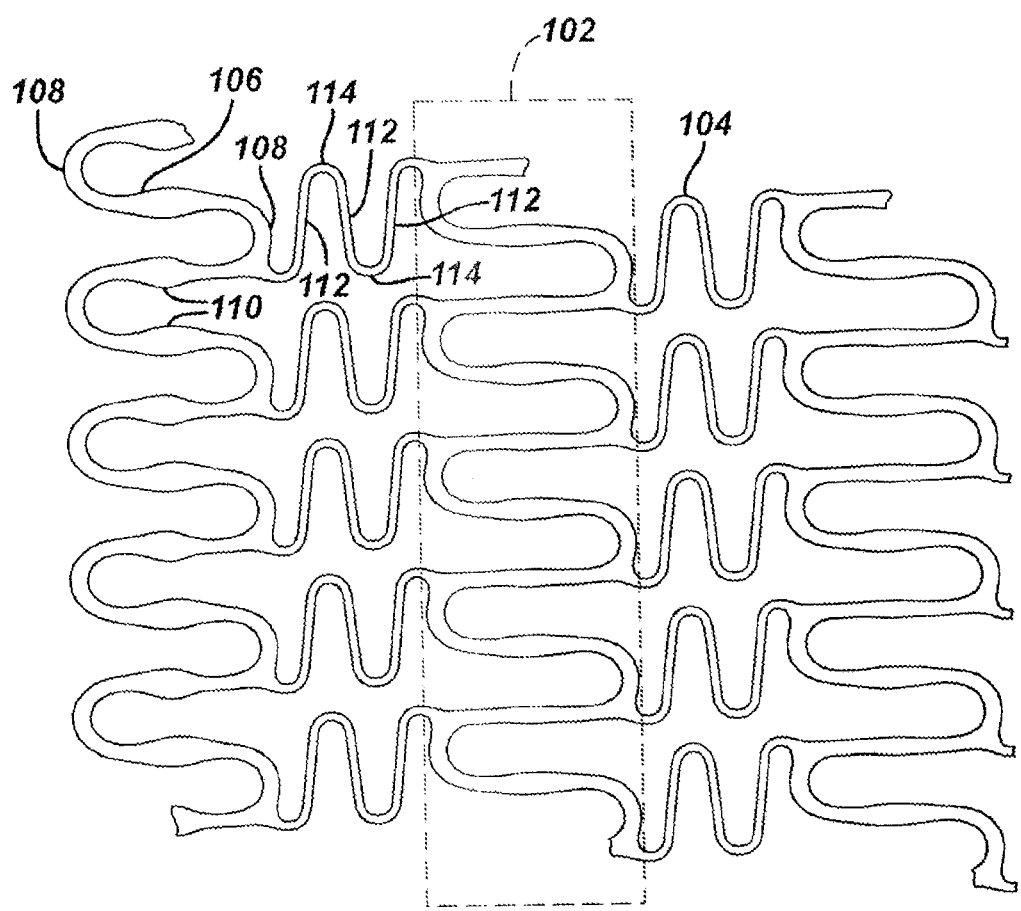
FIG. 3 is a planar representation of an exemplary stent fabricated from biocompatible materials in accordance with the present invention.

Referring to FIG. 3, there is illustrated a partial planar view of an exemplary stent 100 in accordance with the present invention. The exemplary stent 100 comprises a plurality of hoop components 102 interconnected by a plurality of flexible connectors 104. The hoop components 102 are formed as a continuous series of substantially circumferentially oriented radial strut members 106 and alternating radial arc members 108. Although shown in planar view, the hoop components 102 are essentially ring members that are linked together by the flexible connectors 104 to form a substantially tubular stent structure. The combination of radial strut members 106 and alternating radial arc members 108 form a substantially sinusoidal pattern. Although the hoop components 102 may be designed with any number of design features and assume any number of configurations, in the exemplary embodiment, the radial strut members 106 are wider in their central regions 110. This design feature may be utilized for a number of purposes, including, increased surface area for drug delivery.

The flexible connectors 104 are formed from a continuous series of substantially longitudinally oriented flexible strut members 112 and alternating flexible arc members 114. The flexible connectors 104, as described above, connect adjacent hoop components 102 together. In this exemplary embodiment, the flexible connectors 104 have a substantially N-shape with one end being connected to a radial arc member on one hoop component and the other end being connected to a radial arc member on an adjacent hoop component. As with the hoop components 102, the flexible connectors 104 may comprise any number of design features and any number of configurations. In the exemplary embodiment, the ends of the flexible connectors 104 are connected to different portions of the radial arc members of adjacent hoop components for ease of nesting during crimping of the stent. It is interesting to note that with this exemplary configuration, the radial arcs on adjacent hoop components are slightly out of phase, while the radial arcs on every other hoop component are substantially in phase. In addition, it is important to note that not every radial arc on each hoop component need be connected to every radial arc on the adjacent hoop component.

It is important to note that any number of designs may be utilized for the flexible connectors or connectors in an intraluminal scaffold or stent. For example, in the design described above, the connector comprises two elements, substantially longitudinally oriented strut members and flexible arc members. In alternate designs, however, the connectors may comprise only a substantially longitudinally oriented strut member and no flexible arc member or a flexible arc connector and no substantially longitudinally oriented strut member.

The substantially tubular structure of the stent 100 provides the scaffolding for maintaining the patentcy of substantially tubular organs, such as arteries. The stent 100 comprises a luminal surface and an abluminal surface. The distance between the two surfaces defines the wall thickness as is described in detail above. The stent 100 has an unexpanded diameter for delivery and an expanded diameter, which roughly corresponds to the normal diameter of the organ into which it is delivered. As tubular organs such as arteries may vary in diameter, different size stents having different sets of unexpanded and expanded diameters may be designed without departing from the spirit of the present invention. As described herein, the stent 100 may be formed form any number of metallic materials, including cobalt-based alloys, iron-based alloys, titanium-based alloys, refractory-based alloys and refractory metals.

In the exemplary stent described above, a number of examples may be utilized to illustrate the relationship of equiaxed granularity to wall thickness. In the first example, the wall thickness may be varied in the range from about 0.0005 inches to about 0.006 inches for a stent having an expanded inside diameter of less than about 2.5 millimeters. Accordingly, for a maximal number of equiaxed grains, which in the exemplary embodiment is substantially not more than ten (10) discrete grains across the thickness of the wall, the equiaxed grain size shall be equal to or greater than substantially 1.25 microns. This dimensional attribute may be arrived at by simply dividing the minimal available wall thickness by the maximal number of available equiaxed grains. In another example, the wall thickness may be varied in the range from about 0.002 inches to about 0.008 inches for a stent having an expanded inside diameter from about 2.5 millimeters to about 5.0 millimeters. Accordingly, for a maximal number of equiaxed grains, which in the exemplary embodiment is substantially not more than ten (10) discrete grains across the thickness of the wall, the equiaxed grain size shall be equal to or greater than substantially 5.0 microns. In yet another example, the wall thickness may be varied in the range from about 0.004 inches to about 0.012 inches for a stent having an expanded inside diameter from about 5.0 millimeters to about 12.0 millimeters. Accordingly, for a maximal number of equiaxed grains, which in the exemplary embodiment is substantially not more than ten (10) discrete grains across the thickness of the wall, the equiaxed grain size shall be equal to or greater than substantially 10.0 microns. In yet still another example, the wall thickness may be varied in the range from about 0.006 inches to about 0.025 inches for a stent having an expanded inside diameter from about 12.0 millimeters to about 50.0 millimeters. Accordingly, for a maximal number of equiaxed grains, which in the exemplary embodiment is substantially not more than ten (10) discrete grains across the thickness of the wall, the equiaxed grain size shall be equal to or greater than substantially 15.0 microns. In making the above calculations, it is important to maintain rigorous consistency of dimensional units.

Figure 4:
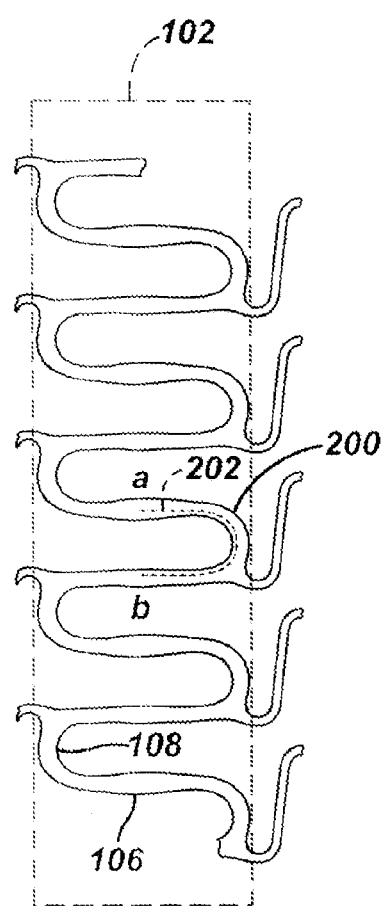
FIG. 4 is a detailed planar representation of a hoop of an exemplary stent fabricated from the biocompatible materials in accordance with the present invention.

In accordance with another aspect of the present invention, the elements of the exemplary stent 100, illustrated in FIG. 3, may be further defined in terms that may be utilized to describe the relationship between geometry, material and the effects of applied loading. Referring to FIG. 4, there is illustrated, in planar view, a single hoop component 102. As described above, the hoop component 102 is formed as a series of substantially circumferentially oriented radial strut members 106 and alternating radial arc members 108. However, the hoop component 102 may also be defined as a number of interconnected loops, wherein a single loop is the element between point a and point b in FIG. 4. In other words, each single loop comprises a portion of two radial strut members and an entire radial arc member. Formulaically, the linear length of a single loop, $L_L$, may be given by $$L_L = RS_L + RA_L, \quad (2)$$

wherein $RS_L$ is the length of a strut member and $RA_L$ is the linear length of the arc member as measured through its center line. Given that the hoop 102 may be defined as a number of interconnected loops, the total linear path length of a hoop, $H_L$, may be given by $$H_L = \Sigma L_L. \quad (3)$$

From the expressions represented by equations (2) and (3) a number of ratios may be developed that describe or define the relationship between geometry, material and the effects of applied load. More specifically, it is the unique material composition and built in properties, i.e. microstructure, that provide the means for fabricating a stent with various geometries that are able to withstand the various loading conditions as is described in detail subsequently. For example, a stent may be designed such that each radial strut's member is configured to exhibit substantially no permanent plastic deformation upon expansion while each radial arc member is configured to accommodate substantially all permanent plastic deformation upon expansion. Alternately, a stent may be designed such that each radial arc member is configured to exhibit substantially no permanent plastic deformation upon expansion, while each radial strut member is configured to accommodate substantially all permanent deformation upon expansion. As these two examples represent the two extremes, it is important to note that the present invention also applies to the continuum between these extremes.

The material properties that are of importance relate to the microstructure as described in detail above. Specifically, the stents are fabricated from a metallic material processed to have a microstructure with a granularity of about thirty-two microns or less and comprise from about two to about ten substantially equiaxed grains as measured across the wall thickness of the stent. The ratios set forth below help describe the desirable properties of the stent.

The expansion efficiency ratio, $H_{\textit{eff}}$, is given by $$H_{\textit{eff}} = C/H_L, \quad (4)$$

wherein C is the circumference of a fully expanded hoop (or stent) and $H_L$ is the total path length of a hoop as set forth in equation (3). Due to the metallic materials and associated built-in properties thereof, the ratio of equation (4) that may be achieved is given by $$H_{\textit{eff}} = C/H_L > 0.25. \quad (5)$$

In other words, the ratio of the circumference of a fully expanded hoop to the total path of the hoop is greater than 0.25. Obviously, the maximum that this ratio may achieve is unity since the path length should not be greater than the circumference of the expanded hoop. However, it is this 0.25 expansion efficiency ratio that is important. In any stent design it is desirable to minimize the amount of structural metal within the vessel and to reduce the overall complexity of fabrication. Expansion efficiency ratios of greater than 0.25 are achievable through the utilization of these new materials. It is important to note that the circumference of a fully expanded hoop should substantially correspond to the normal luminal circumference of the vessel into which the stent is placed. In addition, if the lumen of the vessel is not substantially circular, perimeter may be substituted for circumference, C.

The loop efficiency ratio, $L_{\textit{eff}}$, is given by $$L_{\textit{eff}} = L_L/RA_L, \quad (6)$$

wherein $L_L$ is the linear length or path-length of a single loop given by equation (2) and $RA_L$ is the linear length or path-length of an arc member. Using the elementary rules of algebraic substitution while maintaining rigorous dimensional integrity, Equation (6) may be rewritten as $$L_{\textit{eff}} = (RS_L + RA_L)/RA_L. \quad (7)$$

As may be easily seen from Equation (7), the loop efficiency ratio may never be less than unity. However, because of the material properties, the linear length or path-length of the arc and the linear length or path-length of the struts may be manipulated to achieve the desired characteristics of the final product. For example, under the condition where the strain is primarily carried within the radial arc member, increasing the length of the radial strut for a fixed expansion diameter (displacement controlled phenomena) reduces the magnitude of the non-recoverable plastic strain integrated across the entirety of the radial arc. Similarly, under the condition where the strain is primarily carried within the radial strut member, increasing the length of the radial strut for a fixed expansion diameter (displacement controlled phenomena) reduces the magnitude of the non-recoverable plastic strain integrated across the entirety of the radial strut. In addition, under the condition where the strain is primarily carried within the radial arc member, increasing the path-length of the radial arc for a fixed expansion diameter (displacement controlled phenomena) reduces the magnitude of the non-recoverable plastic strain integrated across the entirety of the radial arc. As these examples represent the extremes, it is important to note that the present invention also applies to the continuum between these extremes.

Accordingly, since the material is able to withstand greater loading, various designs based upon the above ratios may be achieved.

It is important to note that no assumption is made as to the symmetry of the radial struts or radial arc that comprise each single loop and the hoops of the structure. Furthermore, these principals also apply to loops that are interconnected along the longitudinal axis but not necessarily along the radial axis, for example, loops configured into a helical structure. Although a single loop has been illustrated with a single arc member, it obvious to those of ordinary skill in the art, a single loop may be comprise no radial arcs, a single radial arc (as illustrated in FIGS. 3 and 4) and/or multiple radial arcs and no radial strut, a single radial strut and/or multiple radial struts (as illustrated in FIGS. 3 and 4).

Intraluminal scaffolds or stents may comprise any number of design configurations and materials depending upon the particular application and the desired characteristics. One common element of all stent designs is that each stent comprises at least one load-bearing element. Typically, the load-bearing elements have well defined geometries; however, alternate non-conventional geometries may be described in-terms of a bounded cross-sectional area. These bounded areas may be engineered to have either an asymmetric or symmetric configuration. Regardless of the configuration, any bounded cross-sectional area should include at least one internal grain boundary. Those skilled in the art will recognize that the grain-boundary identified in this exemplary embodiment should preferably not constitute any measurable degree of the surface defined by the perimeter of the bounded cross-sectional area. Additionally, those skilled in the art will understand that the grain-boundary discussed in this exemplary embodiment should preferably be characterized as having a high-angle (i.e. typically greater than or equal to about 35 degrees) crystallographic interface. Also, in the presence of microstructural defects such as microcracks (i.e. lattice level discontinuities that can be characterized as planar crystallographic defects), the fatigue crack growth-rate will be expected to be proportional to the number of grains that exist within the bounded cross-sectional area. Since there is one internal grain boundary, this ensures that at least two discrete grains or portions thereof will exist within the bounded cross-sectional area. As described herein, the well-known Hall-Petch relationship that inversely relates grain-size to strength should be observed in this exemplary embodiment as the average grain-size will proportionally decrease as the number of grains within the bounded cross-sectional area increases. In addition, as the number of grains increase within the bounded cross-sectional area, the ability for the microstructure to internally accommodate stress-driven grain boundary sliding events will also increase and should preferably increase localized ductility.

Figure 5:
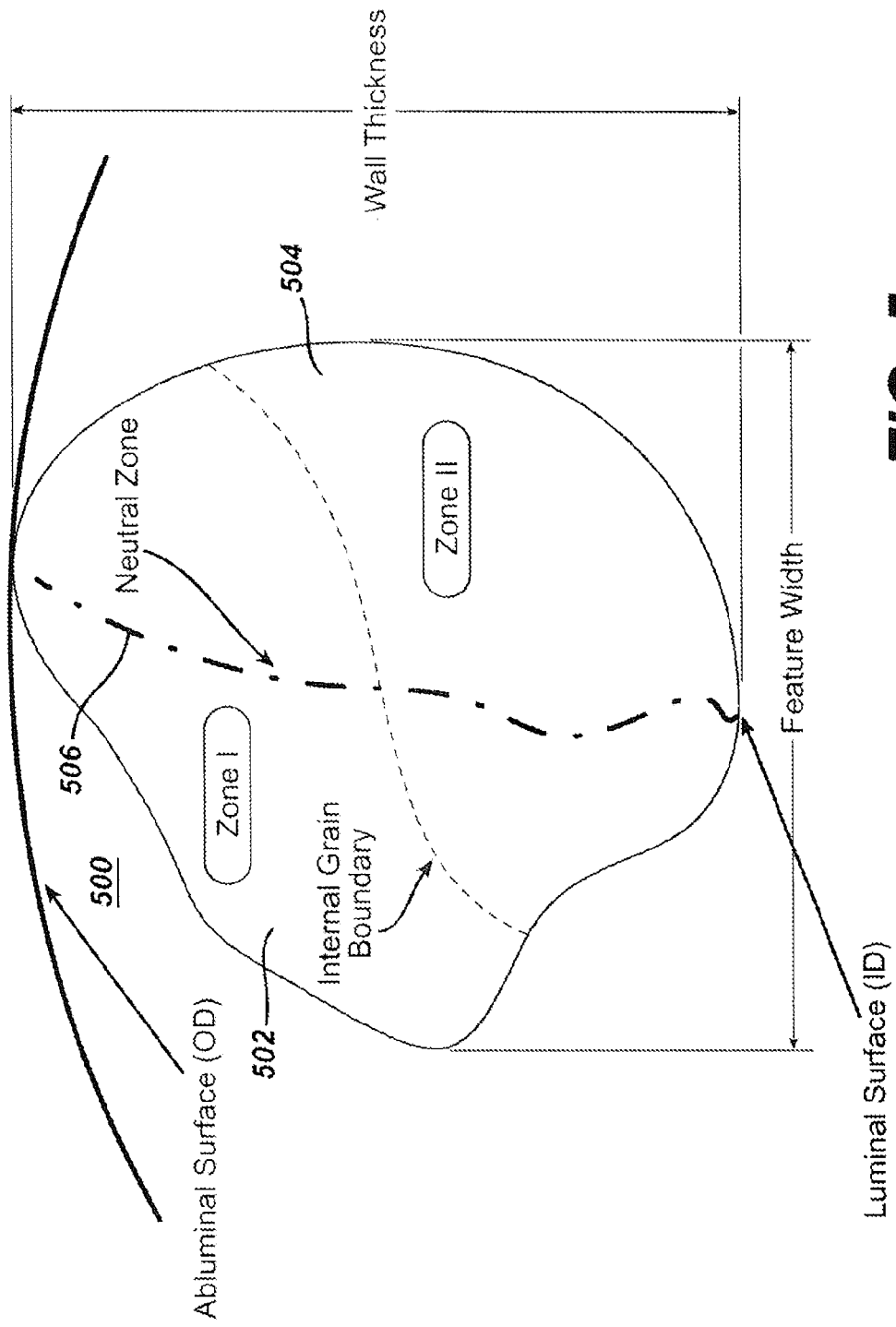
FIG. 5 is a simplified schematic cross-sectional representation of a load bearing intraluminal scaffold element in accordance with the present invention.

Referring to FIG. 5, there is illustrated a cross-sectional representation of a load-bearing stent element 500. As shown, the bounded cross-sectional area comprises a first zone 502, a second zone 504 and a neutral zone 506 which are the result of a stress gradient that is directly proportional to the external loading conditions. The neutral zone 506 is generally defined as a substantially stress free zone that exists between and is bounded by the first zone 502 and the second zone 504. As a function of changing external loading conditions either from the unloaded condition or a loaded condition, the first and second zones, 502 and 504, will undergo a change in tensile and/or compressive stress. It is important to note that the zone assignments shown in FIG. 5 are illustrative in nature and not intended to define relative positioning within the bounded area. The load bearing stent element 500 has a wall thickness that is defined as the radial distance between the luminal surface and the abluminal surface. The load bearing element 500 also has a feature width. The feature width is defined as the linear distance across the first zone 502, neutral zone 506 and the second zone 504 in the direction that is substantially orthogonal to the wall thickness. It is important to note that the feature width is measured at a point that represents the greatest measurable distance in a direction that is substantially orthogonal to the wall thickness.

Other elements of the intraluminal scaffold may be designed in a similar manner, for example, the flexible connectors. While not considered the primary load bearing elements, the flexible connectors undergo longitudinally applied external loading and applied external bending moments.

Figure 6:
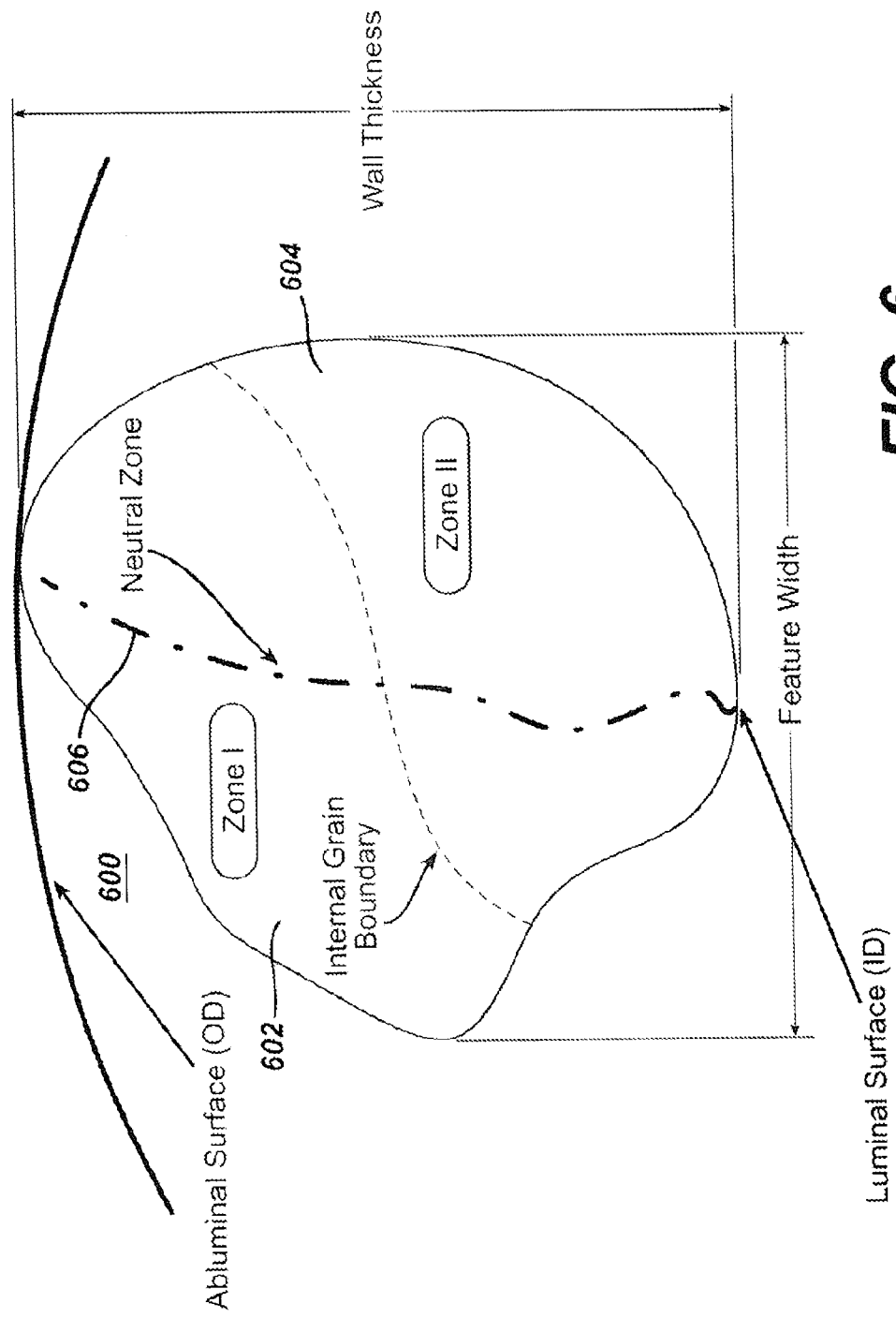
FIG. 6 is a first simplified schematic cross-sectional representation of a flexible connector intraluminal scaffold element in accordance with the present invention.

Referring to FIG. 6, there is illustrated a cross-sectional representation of a flexible connector stent element 600. The flexible connector stent element interconnects the substantially radial load-bearing stent elements or hoop components. The flexible connector stent elements are substantially oriented along the longitudinal axis of the stent. Referring back to FIG. 3, the flexible connector stent elements comprise the flexible connectors 104 which are formed from a continuous series of substantially longitudinally oriented flexible strut members 112 and alternating flexible arc members 114. It is important to note the flexible connector stent elements may comprise a simpler design than described herein, for example, a singular longitudinal oriented strut or arc. As shown, under substantially longitudinal applied external loading conditions, i.e., tensile and compressive the bounded cross-sectional area comprises a first zone 602, a second zone 604 and a neutral zone 606 which are the result of a stress gradient that is directly proportional to these external loading conditions. The neutral zone 606 is generally defined as a substantially stress free zone that exists between and is bounded by the first zone 602 and the second zone 604. As a function of changing external loading conditions either from the unloaded condition or a loaded condition, the first and second zones, 602 and 604, will undergo a change in tensile and/or compressive stress. It is important to note that the zone assignments shown in FIG. 6 are illustrative in nature and not intended to define relative positioning within the bounded area. The flexible connector stent element 600 has a wall thickness that is defined as the radial distance between the luminal surface and the abluminal surface. The flexible connector element 600 also has a feature width. The feature width is defined as the linear distance that is substantially orthogonal to the wall thickness. It is important to note that the feature width is measured at a point that represents the greatest measurable distance in a direction that is substantially orthogonal to the wall thickness.

Figure 7:
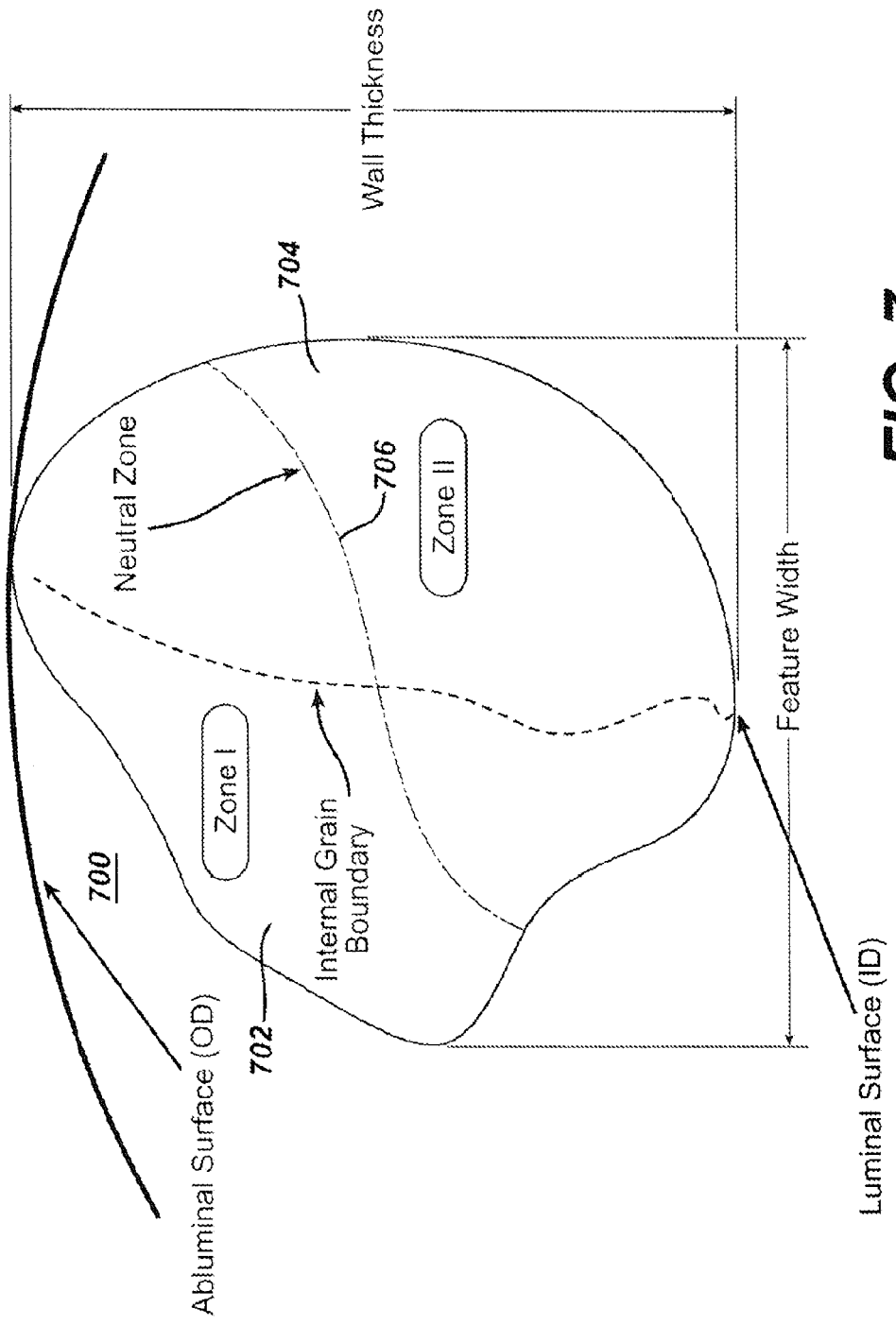
FIG. 7 is a second simplified schematic cross-sectional representation of a flexible connector intraluminal scaffold element in accordance with the present invention.

Referring to FIG. 7, there is illustrated another cross-sectional representation of a flexible connector stent element 700. As shown, under external loading conditions that are substantially comprised of applied bending moments, the bounded cross-sectional area comprises a first zone 702, a second zone 704 and a neutral zone 706 which are the result of a stress gradient that is directly proportional to these external loading conditions. The neutral zone 706 is generally defined as a substantially stress free zone that exists between and is bounded by the first zone 702 and the second zone 704. As a function of changing external loading conditions either from the unloaded condition or a loaded condition, the first and second zones, 702 and 704, will undergo a change in tensile and/or compressive stress. It is important to note that the zone assignments shown in FIG. 7 are illustrative in nature and not intended to define relative positioning within the bounded area. The flexible connector stent element 700 has a wall thickness that is defined as the radial distance between the luminal surface and the abluminal surface. The flexible connector element 700 also has a feature width. The feature width is defined as the linear distance that is substantially orthogonal to the wall thickness. It is important to note that the feature width is measured at a point that represents the greatest measurable distance in a direction that is substantially orthogonal to the wall thickness.

Figure 8:
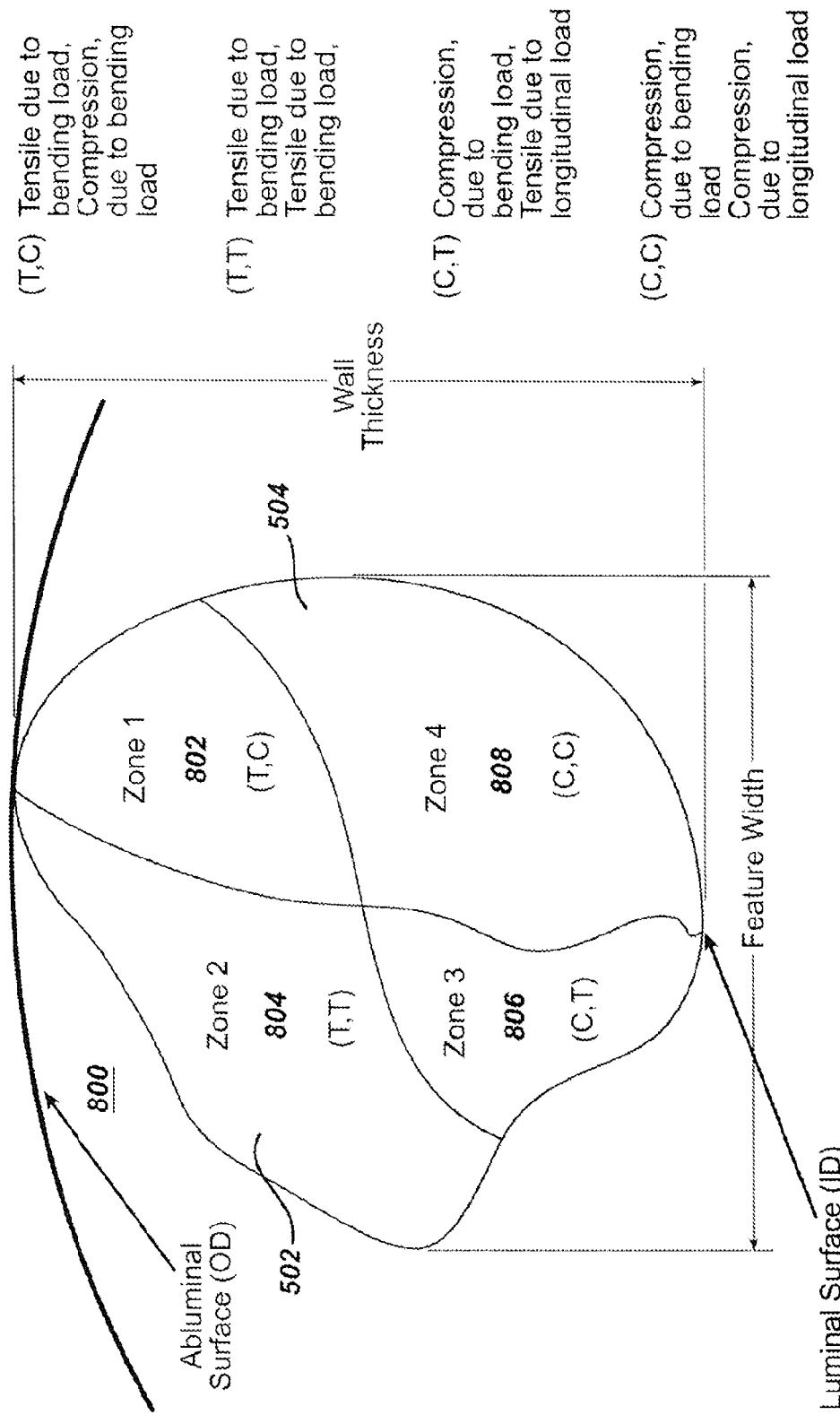
FIG. 8 is a third simplified schematic cross-sectional representation of a flexible connector intraluminal scaffold element in accordance with the present invention.

Referring to FIG. 8, there is yet another illustrated cross-sectional representation of a flexible connector stent element 800. As shown, under external loading conditions that are comprised of blend of applied bending moments and longitudinal applied external loading conditions, the bounded cross-sectional area comprises a first zone 802, a second zone 804, a third zone 806, a fourth zone 808 and an equilibrium zone (not illustrated) which are the result of one or more stress gradients that are directly proportional to these external loading conditions. The equilibrium zone is generally defined as a substantially stress free zone that exists between and is bounded by at least two zones. As a function of changing external loading conditions either from the unloaded condition or a loaded condition, the zones, 802, 804, 806 and/or 808 will undergo changes in tensile and/or compressive stress. It is important to note that the zone assignments shown in FIG. 8 are illustrative in nature and not intended to define relative positioning within the bounded area. The flexible connector stent element 800 has a wall thickness that is defined as the radial distance between the luminal surface and the abluminal surface. The flexible connector element 800 also has a feature width. The feature width is defined as the linear distance that is substantially orthogonal to the wall thickness. It is important to note that the feature width is measured at a point that represents the greatest measurable distance in a direction that is substantially orthogonal to the wall thickness.

The exemplary load bearing stent element 500 and the flexible connector stent elements 600, 700 and 800 that are illustrated in FIGS. 5, 6, 7 and 8 may be fabricated from any of the metallic materials described herein and processed to preferably exhibit a multiplicity of grains when measured across the bounded cross-sectional area defined by the wall thickness and the feature width. When fabricated from a substantially polymeric material system, the properties and attributes described above, that are recognizable by one of appropriate skill and technical qualification in the relevant art, may be utilized to produce a load-bearing structure that is substantially similar to that created with the metallic materials described above.

Accordingly, in yet another exemplary embodiment, an intraluminal scaffold element may be fabricated from a non-metallic material such as a polymeric material including non-crosslinked thermoplastics, cross-linked thermosets, composites and blends thereof. There are typically three different forms in which a polymer may display the mechanical properties associated with solids; namely, as a crystalline structure, as a semi-crystalline structure and/or as an amorphous structure. All polymers are not able to fully crystallize, as a high degree of molecular regularity within the polymer chains is essential for crystallization to occur. Even in polymers that do substantially crystallize, the degree of crystallinity is generally less than 100 percent. Within the continuum between fully crystalline and amorphous structures, there are two thermal transitions possible; namely, the crystal-liquid transition (i.e. melting point temperature, $T_m$) and the glass-liquid transition (i.e. glass transition temperature, $T_g$). In the temperature range between these two transitions there may be a mixture of orderly arranged crystals and chaotic amorphous polymer domains.

The Hoffman-Lauritzen theory of the formation of polymer crystals with "folded" chains owes its origin to the discovery in 1957 that thin single crystals of polyethylene may be grown from dilute solutions. Folded chains are preferably required to form a substantially crystalline structure. Hoffman and Lauritzen established the foundation of the kinetic theory of polymer crystallization from "solution" and "melt" with particular attention to the thermodynamics associated with the formation of chain-folded nuclei.

Crystallization from dilute solutions is required to produce single crystals with macroscopic perfection (typically magnifications in the range of about 200× to about 400×). Polymers are not substantially different from low molecular weight compounds such as inorganic salts in this regard. Crystallization conditions such as temperature, solvent and solute concentration may influence crystal formation and final form. Polymers crystallize in the form of thin plates or "lamellae." The thickness of these lamellae is on the order of 10 nanometers (i.e. nm). The dimensions of the crystal plates perpendicular to the small dimensions depend on the conditions of the crystallization but are many times larger than the thickness of the platelets for a well-developed crystal. The chain direction within the crystal is along the short dimension of the crystal, which indicates that, the molecule folds back and forth (e.g. like a folded fire hose) with successive layers of folded molecules resulting in the lateral growth of the platelets. A crystal does not consist of a single molecule nor does a molecule reside exclusively in a single crystal. The loop formed by the chain as it emerges from the crystal turns around and reenters the crystal. The portion linking the two crystalline sections may be considered amorphous polymer. In addition, polymer chain ends disrupt the orderly fold patterns of the crystal, as described above, and tend to be excluded from the crystal. Accordingly, the polymer chain ends become the amorphous portion of the polymer. Therefore, no currently known polymeric material can be 100 percent crystalline. Post polymerization processing conditions dictate the crystal structure to a substantial extent.

Single crystals are not observed in crystallization from bulk processing. Bulk crystallized polymers from melt exhibits domains called "spherulites" that are symmetrical around a center of nucleation. The symmetry is perfectly circular if the development of the spherulite is not impinged by contact with another expanding spherulite. Chain folding is an essential feature of the crystallization of polymers from the molten state. Spherulites are composed of aggregates of "lamellar" crystals radiating from a nucleating site. Accordingly, there is a relationship between solution and bulk grown crystals.

The spherical symmetry develops with time. Fibrous or lathlike crystals begin branching and fanning out as in dendritic growth. As the lamellae spread out dimensionally from the nucleus, branching of the crystallites continue to generate the spherical morphology. Growth is accomplished by the addition of successive layers of chains to the ends of the radiating laths. The chain structure of polymer molecules suggests that a given molecule may become involved in more than one lamella and thus link radiating crystallites from the same or adjacent spherulites. These interlamellar links are not possible in spherulites of low molecular weight compounds, which show poorer mechanical strength as a consequence.

The molecular chain folding is the origin of the "Maltese" cross, which identifies the spherulite under crossed polarizers. For a given polymer system, the crystal size distribution is influenced by the initial nucleation density, the nucleation rate, the rate of crystal growth, and the state of orientation. When the polymer is subjected to conditions in which nucleation predominates over radial growth, smaller crystals result. Larger crystals will form when there are relatively fewer nucleation sites and faster growth rates. The diameters of the spherulites may range from about a few microns to about a few hundred microns depending on the polymer system and the crystallization conditions.

Therefore, spherulite morphology in a bulk-crystallized polymer involves ordering at different levels of organization; namely, individual molecules folded into crystallites that in turn are oriented into spherical aggregates. Spherulites have been observed in organic and inorganic systems of synthetic, biological, and geological origin including moon rocks and are therefore not unique to polymers.

Stress induced crystallinity is important in film and fiber technology. When dilute solutions of polymers are stirred rapidly, unusual structures develop which are described as having "shish kebab" morphology. These consist of chunks of folded chain crystals strung out along a fibrous central column. In both the "shish" and the "kebab" portions of the structure, the polymer chains are parallel to the overall axis of the structure.

When a polymer melt is sheared and quenched to a thermally stable condition, the polymer chains are perturbed from their random coils to easily elongate parallel to the shear direction. This may lead to the formation of small crystal aggregates from deformed spherulites. Other morphological changes may occur, including spherulite to fibril transformation, polymorphic crystal formation change, reorientation of already formed crystalline lamellae, formation of oriented crystallites, orientation of amorphous polymer chains and/or combinations thereof.

It is important to note that polymeric materials may be broadly classified as synthetic, natural and/or blends thereof. Within these broad classes, the materials may be defined as biostable or biodegradable. Examples of biostable polymers include polyolefins, polyamides, polyesters, fluoropolymers, and acrylics. Examples of natural polymers include polysaccharides and proteins. Examples of biodegradable polymers include the family of polyesters such as polylactic acid, polyglycolic acid, polycaprolactone, polytrimethylene carbonate and polydioxanone. Additional examples of biodegradable polymers include polyhydroxyalkanoates such as polyhydroxybutyrate-co-valerates; polyanhydrides; poly-orthoesters; polyaminoacids; polyesteramides; polyphosphoesters; and polyphosphazenes. Copolymers and blends of any of the described polymeric materials may be utilized in accordance with the present invention.

When constructing an intraluminal stent from metallic materials, a maximum granularity of about 32 microns or less was necessary to achieve the functional properties and attributes described herein. When constructing an intraluminal stent from polymeric materials, a maximum spherulitic size of about 50 microns or less was necessary to achieve the functional properties and attributes described herein.

The local delivery of therapeutic agent/therapeutic agent combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any other type of medical device may be coated in some fashion with a drug or drug combination, which enhances treatment over use of the singular use of the device or pharmaceutical agent.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagines); antiplatelet agents such as $G(GP)$ $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine and cytarabine) purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory; such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalec), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrozone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors, antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In accordance with another exemplary embodiment, the stents described herein, whether constructed from metals or polymers, may be utilized as therapeutic agents or drug delivery devices. The metallic stents may be coated with a biostable or bioabsorbable polymer or combinations thereof with the therapeutic agents incorporated therein. Typical material properties for coatings include flexibility, ductility, tackiness, durability, adhesion and cohesion. Biostable and bioabsorbable polymers that exhibit these desired properties include methacrylates, polyurethanes, silicones, polyvinylacetates, polyvinylalcohol, ethylenevinylalcohol, polyvinylidene fluoride, poly-lactic acid, poly-glycolic acid, polycaprolactone, polytrimethylene carbonate, polydioxanone, polyorthoester, polyanhydrides, polyphosphoester, polyaminoacids as well as their copolymers and blends thereof.

In addition to the incorporation of therapeutic agents, the coatings may also include other additives such as radiopaque constituents, chemical stabilizers for both the coating and/or the therapeutic agent, radioactive agents, tracing agents such as radioisotopes such as tritium (i.e. heavy water) and ferromagnetic particles, and mechanical modifiers such as ceramic microspheres as will be described in greater detail subsequently. Alternatively, entrapped gaps may be created between the surface of the device and the coating and/or within the coating itself. Examples of these gaps include air as well as other gases and the absence of matter (i.e. vacuum environment). These entrapped gaps may be created utilizing any number of known techniques such as the injection of microencapsulated gaseous matter.

As described above, different drugs may be utilized as therapeutic agents, including sirolimus, heparin, everolimus, tacrolimus, paclitaxel, cladribine as well as classes of drugs such as statins. These drugs and/or agents may be hydrophilic, hydrophobic, lipophilic and/or lipophobic. The type of agent will play a role in determining the type of polymer. The amount of the drug in the coating may be varied depending on a number of factors including, the storage capacity of the coating, the drug, the concentration of the drug, the elution rate of the drug as well as a number of additional factors. The amount of drug may vary from substantially zero percent to substantially one hundred percent. Typical ranges may be from about less than one percent to about forty percent or higher. Drug distribution in the coating may be varied. The one or more drugs may be distributed in a single layer, multiple layers, single layer with a diffusion barrier or any combination thereof.

Different solvents may be used to dissolve the drug/polymer blend to prepare the coating formulations. Some of the solvents may be good or poor solvents based on the desired drug elution profile, drug morphology and drug stability.

There are several ways to coat the stents that are disclosed in the prior art. Some of the commonly used methods include spray coating; dip coating; electrostatic coating; fluidized bed coating; and supercritical fluid coatings.

Some of the processes and modifications described herein that may be used will eliminate the need for polymer to hold the drug on the stent. Stent surfaces may be modified to increase the surface area in order to increase drug content and tissue-device interactions. Nanotechnology may be applied to create self-assembled nanomaterials that can contain tissue specific drug containing nanoparticles. Microstructures may be formed on surfaces by microetching in which these nanoparticles may be incorporated. The microstructures may be formed by methods such as laser micromachining, lithography, chemical vapor deposition and chemical etching. Microstructures have also been fabricated on polymers and metals by leveraging the evolution of micro electro-mechanical systems (MEMS) and microfluidics. Examples of nanomaterials include carbon nanotubes and nanoparticles formed by sol-gel technology. Therapeutic agents may be chemically or physically attached or deposited directly on these surfaces. Combination of these surface modifications may allow drug release at a desired rate. A top-coat of a polymer may be applied to control the initial burst due to immediate exposure of drug in the absence of polymer coating.

As described above, polymer stents may contain therapeutic agents as a coating, e.g. a surface modification. Alternatively, the therapeutic agents may be incorporated into the stent structure, e.g. a bulk modification that may not require a coating. For stents prepared from biostable and/or bioabsorbable polymers, the coating, if used, could be either biostable or bioabsorbable. However, as stated above, no coating may be necessary because the device itself is fabricated from a delivery depot. This embodiment offers a number of advantages. For example, higher concentrations of the therapeutic agent or agents may be achievable. In addition, with higher concentrations of therapeutic agent or agents, regional delivery is achievable for greater durations of time.

In yet another alternate embodiment, the intentional incorporation of ceramics and/or glasses into the base material may be utilized in order to modify its physical properties. Typically, the intentional incorporation of ceramics and/or glasses would be into polymeric materials for use in medical applications. Examples of biostable and/or bioabsorbable ceramics or/or glasses include hydroxyapatite, tricalcium phosphate, magnesia, alumina, zirconia, yttrium tetragonal polycrystalline zirconia, amorphous silicon, amorphous calcium and amorphous phosphorous oxides. Although numerous technologies may be used, biostable glasses may be formed using industrially relevant sol-gel methods. Sol-gel technology is a solution process for fabricating ceramic and glass hybrids. Typically, the sol-gel process involves the transition of a system from a mostly colloidal liquid (sol) into a gel.

In accordance with another exemplary embodiment, an intraluminal scaffold may be configured such that the principal radial load bearing elements are fabricated from metallic materials and the flexible connectors are fabricated from polymeric materials. Within this construct are a number of structural, surface and/or geometric variations. In one exemplary embodiment, the hoops 102, as illustrated in FIGS. 3 and 4, may be fabricated from any metallic materials such as those described herein, and the flexible connectors 104 may be fabricated from any bioabsorbable polymer described herein.

In another exemplary embodiment, the hoops 102 may be fabricated from any metallic materials such as those described herein, and the flexible connectors 104 may be fabricated from any bioabsorbable polymer described herein and comprise one or more therapeutic agents. These one or more therapeutic agents may be applied onto the surface of the flexible connectors or incorporated into the bulk of the flexible connectors as described herein. In the case of a surface application, the one or more therapeutic agents may be applied without a polymer, with the same polymer or with a different polymer. In this exemplary embodiment, the one or more therapeutic agents may be homogeneously distributed, preferentially distributed or heterogeneously distributed.

In yet another exemplary embodiment, the hoops 102 may be fabricated from any metallic materials such as those described herein and coated with a polymeric material containing one or more therapeutic agents, and the flexible connectors 104 may be fabricated from any bioabsorbable polymer described herein.

In yet another exemplary embodiment, the hoops 102 may be fabricated from any metallic materials such as those described herein and coated with a polymeric material containing one or more therapeutic agents, and the flexible connectors 104 may be fabricated from any bioabsorbable polymer described herein and comprise one or more therapeutic agents. These one or more therapeutic agents may be applied onto the surface of the flexible connectors or incorporated into the bulk of the flexible connectors. In the case of a surface application, the one or more therapeutic agents may be applied without a polymer, with the same polymer or with a different polymer. In this exemplary embodiment, the one or more therapeutic agents may be homogeneously distributed, preferentially distributed or heterogeneously distributed.

In yet another exemplary embodiment, the hoops 102 may be constructed as a structural combination of metallic and polymeric materials. For example, in one instance, the hoop 102 may have a metallic core and a polymeric outer structure. Alternately, the hoop 102 may have a polymeric core and a metallic outer structure. If the metallic outer structure completely encapsulates the polymeric core, the polymeric core should preferably comprise a non-bioabsorbable polymer. If however the polymeric core is not completely encapsulated, then the polymeric core may comprise a bioabsorbable polymer. In another instance, the metals and polymers may be structurally stratified to form the hoops 102.

The advantages of combining polymers and metals and/or metal alloys to prepare medical devices, such as stents, include improved longitudinal and flexural flexibility, higher radial strength, lower recoil and higher radiopacity. In addition, the polymer sections may provide for higher drug loading. The polymer and metal components may be mixed and combined in different ways, for example, rings, connectors and links, to provide greater design flexibility. In addition, the present invention also provides ways to deliver one or more therapeutic agents that are incorporated in the bioabsorbable polymer matrix. Also, the metal portions of the stent may also absorb or degrade with time so that the stent is completely bioabsorbable. There are several ways to prepare polymer-metal composites or hybrids for medical devices.

There are recent patents and patent applications on hybrid intravascular stents (US Patent Application Publication Number 2004/0127970, US Patent Application Publication Number 2004/0199242, U.S. Pat. No. 6,770,089, U.S. Pat. No. 6,565,599, U.S. Pat. No. 6,805,705 and U.S. Pat. No. 6,866,805). In these patents and patent applications, there are metal rings that are connected by polymeric links that provide improved stent deliverability due to lower profile and stent flexibility. The rings and polymer links are connected by different ways such as welding, threading, and chemical means. Typical polymers used to prepare the links are flexible synthetic and water-soluble materials. In one application, bioabsorbable polymers are also utilized in the construction of the links. The rings are made from metals such as stainless steel, cobalt-chromium, nickel-titanium, tantalum and platinum. These stents may also be coated with one or more therapeutic agents.

Drug delivery devices may be developed that are disease specific and for applications such as local and regional drug therapy. The delivery mechanism should provide extended drug release from a controlled system with preferably zero order drug release. The device should also have mechanical integrity that is retained during the active drug delivery phase. Preferably, the device should begin to disappear or degrade after drug delivery and the mechanical need for the device to provide stability passes. The selection of material and design for the device is important, as it should not promote any tissue interaction and have good biocompatibility with minimum inflammation during polymer degradation. It is preferable that the devices may be delivered percutaneously using either balloon or self-expanding delivery system.

Figure 9:
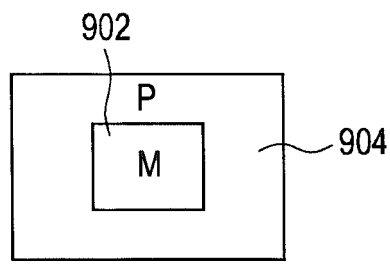
FIG. 9 is a cross-sectional view of a composite element in accordance with the present invention.

In a preferred exemplary embodiment, one or more of the elements of any of the devices disclosed herein, for example, the stent illustrated in FIGS. 3 and 4 may be constructed as a composite structure. In this preferred exemplary embodiment, the composite structure comprises a metallic core that is encapsulated by a polymeric material or system that forms an outer layer, structure or shell. FIG. 9 illustrates the composite structure in accordance with the present invention. The metallic core 902 in this preferred exemplary embodiment is not degradable or bioabsorbable and may comprise any of the metallic materials described herein. The polymeric material or system 904 in this preferred exemplary embodiment comprises a bioabsorbable polymer or combination of polymers as described herein. Accordingly, after a given amount of time, the outer polymeric material or system will be gone leaving only the inner metallic structure. This design offers a number of advantages, including higher radial stiffness, lower radial recoil, improved radiopacity as compared to pure polymeric stents and lower profile as compared to pure polymeric stents.

The selection criteria for the polymer system should include factors such as the degradation time (weeks, months or years), whether or not the material will promote embolization during degradation, the retention of short term and long term mechanical properties, the ability to customize the properties using composite structures and blends, the capability of being processed in to different structures by variety of processing methods, no issues with drug-polymer interaction and long term stability, the ability to make the polymer radiopaque either by adding an additive or by synthesizing the additive in the polymer backbone, the minimization of tissue inflammation before and after polymer absorption and an easier regulatory pathway for using it in a vascular environment.

The type of polymers that may be used to prepare the devices and stents may degrade via different mechanisms such as bulk or surface erosion. Drug delivery may be "controlled" if drug release is determined by the kinetics of polymer erosion rather than drug diffusion. The degradation mechanism may be controlled either by bulk or surface erosion of the polymer. Surface erodible polymers are typically hydrophobic with water labile linkages. Hydrolysis occurs fast on the surface with no water penetration in the bulk. So the advantages for these polymers are that the drug release rate may be varied linearly while maintaining mechanical integrity. The disadvantages of such materials are low initial strength and are not commercially available. Some examples of surface erodible polymers include polyanhydrides [examples: poly (carboxyphenoxy hexane-sebacic acid), poly (fumaric acid-sebacic acid), poly (carboxyphenoxypropane-sebacic acid), poly (imide-sebacic acid) (50-50), poly (imide-carboxyphenoxy hexane) (33-67)] and polyorthoesters (diketene acetal based polymers)].

Bulk erodible polymers are typically hydrophilic in nature with water labile linkages. Hydrolysis occurs at uniform rates across the polymer matrix. The advantages of such polymers are superior initial strength, good history for its use in different implants and these polymers are readily available. These polymers may lead to initial burst in drug release during breakdown of the polymer matrix during absorption. A family of aliphatic polyesters is most widely used in this class of material. Bulk erodible polymers include poly (α-hydroxy esters) such as poly (lactic acid), poly (glycolic acid), poly (caprolactone), poly (p-dioxanone), poly (trimethylene carbonate), poly (oxaesters), poly (oxaamides), and their copolymers and blends. Some examples of commercially available products from these polymers include poly (dioxanone) [PDS suture], poly (glycolide) [Dexon suture], poly (lactide)-PLLA [bone repair], poly (lactide/glycolide) [Vicryl (10/90) and Panacryl (95/5) sutures], poly (glycolide/caprolactone 75/25) [Monocryl suture] and poly (glycolide/trimethylene carbonate) [Maxon suture].

Other bulk erodible polymers include tyrosine derived poly amino acid [examples: poly (DTH carbonates), poly (arylates), poly (imino-carbonates)], phosphorous containing polymers [e.g., poly (phosphoesters) and poly (phosphazenes)], poly (ethylene glycol) [PEG] based block copolymers [PEG-PLA, PEG-poly (propylene glycol), PEG-poly (butylene terephthalate)], poly (α-malic acid), poly (ester amide), and polyalkanoates [examples: poly (hydroxybutyrate (HB) and poly (hydroxyvalerate) (HV) copolymers].

The devices may be made from combinations of bulk and surface erodible polymers to control the degradation mechanism and drug release as a function of time. Different ways may be used to combine these materials. One way is to prepare blends of two or more polymers to achieve the desired physical and drug release properties. Alternatively, a device may be made from bulk erodible polymer, which is then coated with a drug containing surface erodible polymer. The thickness of the coating may be high so that high drug loadings can be achieved. The thickness of the bulk erodible polymer may be made sufficiently high to maintain physical properties of the device after the drug and surface erodible material has disappeared from the device. This layered approach incorporates the benefits of the two polymer systems to optimize the drug delivery device.

A theoretical model has been developed that allows predicting the erosion mechanism of water insoluble bioabsorbable polymer matrices. The model shows that all degradable polymers may undergo surface or bulk erosion. Erosion of the polymer matrix depends on the diffusivity of water inside the matrix, degradation rate of the polymer's functional groups and the matrix dimensions. Based on these parameters, the model calculates a dimensionless erosion number ($\epsilon$) for a polymer matrix. This number indicates the mode of erosion. A critical device dimension $L_{critical}$ may be calculated from $\epsilon$. Below the critical dimension $L_{critical}$ a polymer matrix will always undergo bulk erosion while above $L_{critical}$, it will be a surface eroding material. For example, polyanhydrides were found to be surface eroding down to a size of approximately $L_{critical}$=75 microns while poly (α-hydroxy esters) matrices need to be larger than $L_{critical}$=7.4 cm to lose their bulk erosion properties.

Shape memory is the ability of a material to remember its original shape, either after mechanical deformation, which is a one-way effect, or by cooling and heating which is a two-way effect. This phenomenon is based on a structural phase transformation. The first materials to have these properties were shape memory metal alloys including TiNi (Nitinol), CuZnAl, and FeNiAl alloys. The structure phase transformation of these materials is known as martensitic transformation. These materials have been proposed for various uses, including vascular stents and guidewires. Shape memory polymers (SMPs) are being developed to replace or augment the use of shape memory alloys mainly because polymers are light, high in shape memory recovery ability, easy to manipulate and more economical compared to shape memory alloys. SMPs are characterized as phase segregated linear block co-polymers having a hard segment and soft segment. The hard segment is typically crystalline with a defined melting point, and the soft segment is typically amorphous with a defined glass transition temperature. The transition temperature of the soft segment is substantially less than the transition temperature of the hard segment.

When the SMP is heated above the melting point of the hard segment, the material may be shaped. This "original" shape may be memorized by cooling the SMP below the melting point of the hard segment. When the shaped SMP is cooled below the glass transition temperature of the soft segment while the shaped is deformed, a new "temporary" shape is fixed. The original shape is recovered by heating the material above the glass transition temperature of the soft segment but below the melting point of the hard segment. The recovery of the original shape induced by an increase of temperature is called the thermal shape memory effect. Several physical properties of SMPs other than ability to memorize shape are significantly altered in response to external changes in temperature and stress, particularly at the glass transition of the soft segment. These properties include elastic modulus, hardness, and flexibility. The modulus of SMP may change by a factor of up to 200 when heated above the glass transition temperature of the soft segment.

SMPs may be biostable and bioabsorbable. Biostable SMPs are generally polyurethanes, polyethers, polyacrylates, polyamides, polysiloxanes, and their copolymers. Bioabsorbable SMPs are relatively new and comprise thermoplastic and thermoset materials. Shape memory thermosets may include poly (caprolactone) dimethyacrylates; and shape memory thermoplastics may include poly (caprolactone) as the soft segment and poly (dioxanone) as the hard segment. These polymers may be used for preparing balloon and self-expanding vascular stents.

Most of the bioabsorbable materials are very brittle with high modulus and low toughness. So, these will be preferable for applications that require high physical properties such as orthopedic implants, sutures, vascular stents and grafts, and other applications known in the art. In order to use these materials for applications that require high ductility and toughness, the polymer properties needs to be modified. These modifications may be achieved by changing either the chemical structure of the polymer backbone or by creating composite structures by blending them with different polymers and plasticizers. The selection of the type of materials for blends or plasticizers is critical as these should be compatible to the main polymer system. The addition of these materials will lower the ability for the polymer to crystallize and depress the glass transition temperature. This will make the blend less stiff and more ductile.

Preparing copolymers with materials that are soft and amorphous may also modify the properties of the polymer. For example, poly (glycolide) is a very stiff material and poly (caprolactone) is a soft and waxy material. So, preparing copolymers from these two polymers [e.g, poly (glycolide-co-caprolactone)] will make the copolymer elastomeric with no crystallinity and high ductility. These copolymers may also be blended with other stiff polymers [e.g., poly (lactic acid) or poly (lactic acid-co-glycolic acid] to modify the overall properties of the stiff material. Stiff polymers may also be blended with SMPs due to their elastomeric properties.

The improved visibility of catheters, guidewires and stents under fluoroscopy is a highly important property to surgeons or cardiologists who must accurately determine device location and orientation.

All processes for improving device visibility on fluoroscopes are based on incorporating a material that absorbs the radiational energy of the x-rays. This material is added to the device in the form of a layer, coating, band, or powder, depending on the nature of the process. There are three primary considerations in adding a radiopaque marker. First, the additive should not add significant stiffness to the device. A good example is the guiding catheter, which needs to be flexible so it may bend and turn as it is maneuvered through the artery. A second important consideration is that the material being added to the device is biocompatible to reduce the possibility of adverse tissue reactions in the body. Inert noble metals such as gold, platinum, iridium, palladium, and rhodium are well recognized for their biocompatibility. A third consideration is that the radiopaque additive must adhere well in the device without the possibility of peeling or delamination. Catheters, and especially stents, may be severely flexed, and the adhesion between the additive and the device must be able to withstand these forces.

An early method of marking catheters involved crimping metal bands at selected points so that the practitioners could see the location of the device. Another way of achieving visibility is by loading the device with a metal powder. Barium is most often used as the metallic element, although tungsten and other fillers are also appearing on the market. Radiopaque coatings may also achieve good results with less impact on the physical characteristics (size, weight, flexibility, etc.) or performance of the device. Radiopaque coatings may be applied to catheters and stents using methods such as chemical vapor deposition (CVD), physical vapor deposition (PVD), electroplating, a high-vacuum deposition process, microfusion process, spray coating, dip coating, electrostatic coating and other coating and surface modification processes known in the art. The coating processes may be used to apply radiopaque additives in selected locations on the device to create discrete bands near the tips of a catheter and stents to provide markers of precise lengths and widths. Such bands can be used as an in-situ "ruler" to more accurately determines the size of vascular lesions, potentially reducing any unnecessary use of multiple stents.

Since polymers are not generally highly radiopaque, the bioabsorbable polymer compositions to prepare the stents and devices should preferably include additives to make the device radiopaque. Radiopaque additives may include inorganic fillers (examples: barium sulfate, bismuth subcarbonate, bismuth oxide, iodine compounds), metal powders (examples: tantalum, gold), metal alloys that consist of gold, platinum, iridium, palladium, rhodium, or a combination of these and other materials well known in the art. The particle size of these fillers may vary from nanometers to microns. The amount of radiopaque additive in the formulation may vary from about one to fifty percent (wt %). The polymer formulations may be prepared by melt or solution processing. Since the density of these additives is very high, sedimentation could occur in the formulation prepared from solutions. Well known dispersion techniques such as high shear mixing, the addition of surfactants and lubricants, viscosity control, surface modification of the additive, small particle size, uniform particle size distribution, shape of the particles of the additive, and other methods known in the formulation art. These additives may be either uniformly distributed in the device or may be preferentially added to sections of the device to make them appear as marker bands. The advantages of the latter approach are that the bands may be markers for the device without interfering with the lesion size and location, it may not have any adverse effect on the device performance (radial strength, etc) and small quantities may be used per device that may prevent any adverse effect on the tissue during its release from the matrix. These bands may be prepared by several ways as described earlier.

The devices may be prepared by conventional polymer processing methods in melt condition including extrusion, co-extrusion, fiber spinning, injection molding, compression molding and in solution condition including fiber spinning (dry and wet spinning), electrostatic fiber spinning, cast films, spinning disk (thin films with uniform thickness), and lyophilization. Different geometries and structures may be formed by different processes including tubes, fibers, microfibers, thin and thick films, discs, foams, microspheres, and intricate geometries. The melt or solution-spun fibers, films and tubes may be further converted to different designs (helical, tubular, slide and lock, etc) and structures by braiding and laser processing. Different methods may also be combined to optimize the performance of the device.

Low temperature fabrication processes are preferred especially when the device contains drugs that are not stable at high temperatures. Some of the preferred processes are solution processing and supercritical fluid processing which includes solvent extraction, coating, extrusion and injection molding. For drugs or agents with high temperature stability, it may be incorporated or encapsulated in the polymer matrix by different melt processing methods. The melt compounded polymer and drug blend may then be converted to different geometry such as fibers, discs/rings, and tubes.

Different processing methods may change the performance of device/geometry for a given polymer. For example, tubes prepared from a rigid polymer will be very stiff when melt extruded but will be very flexible when prepared by electrostatic spinning or lyophilization. This is due to the physical structure of the geometry that is dictated by the process. In the former case, the tubes are solid and in the latter case the tubes are porous. This difference in microstructure may be used to prepare different devices with a desired property.

Processing the materials in different way may generate different morphological changes in the polymer. Stress induced crystallinity is important in film and fiber technology. When dilute solutions of polymers are stirred rapidly, unusual structures develop which are described as having "shish kebab" morphology. These consist of chunks of folded chain crystals strung out along a fibrous central column. In both the "shish" and the "kebab" portions of the structure, the polymer chains are parallel to the overall axis of the structure.

When a polymer melt is sheared and quenched to a thermally stable condition, the polymer chains are perturbed from their random coils to easily elongate parallel to the shear direction. This may lead to the formation of small crystal aggregates from deformed spherulites. Other morphological changes may occur, including spherulite to fibril transformation, polymorphic crystal formation change, reorientation of already formed crystalline lamellae, formation of oriented crystallites, orientation of amorphous polymer chains and/or combinations thereof.

Polymer morphology (amorphous and crystalline) and microstructure (e.g., porous, uniform, etc) is controlled by the way the material is processed and will eventually influence the physical properties of the device. In the case of bioabsorbable polymers, it will change the degradation profile of a material. Amorphous materials degrade faster than crystalline materials, as the amorphous polymer chains are more accessible to hydrolysis than the crystalline domains. Porous structure will degrade faster than a nonporous structure due to differences in surface area. Therefore, drug delivery devices may be prepared by combining structure-property relationships of different materials and processes to achieve a desired performance to meet different therapeutic needs.

The bioabsorbable compositions to prepare devices and stents may also include therapeutic agents. The amount of drug can range from about one to fifty percent (% weight of device). Drugs and or agents may be incorporated in the device by different ways. Drugs and or agents may be coated on the bioabsorbable stent, which may not contain drug (similar to coating metal stents). Polymers used to prepare the coatings are bioabsorbable materials. Drugs and or agents may be incorporated in the stent matrix uniformly so that the amount of drug is higher than a drug coating. These approaches may be combined to optimize the device performance. The stent may preferably carry more drug (1 to 8 mg) than a polymer-coated (100 to 200 microgram) stent as the drug is distributed throughout the device. The drug will release by diffusion and during degradation of the stent. The amount of drug release will be for a longer period of time to treat local and diffuse lesions; and for regional delivery for arterial branches to treat diseases such as vulnerable plaque.

Different types of drugs may be used as therapeutic agents that include cytostatic and cytotoxic agents. Some examples are heparin, sirolimus, everolimus, tacrolimus, biolimus, paclitaxel, statins and cladribine as described in detail herein. These drugs may be hydrophilic or hydrophobic.

The devices may be percutaneously delivered by different methods including balloon expandable (without and with heat), self-expanding (without and with a slideable sheath); combination of balloon and self-expanding systems; and other known methods in the art. Alternately, the devices may also be implanted by surgical procedures. The selection of the delivery system will depend on the device design and delivery site (coronary, periphery, etc).

In the case of a stent comprised of bioabsorbable polymeric materials formed by tubes from solution, the viscosity of the polymer solution will determine the processing method used to prepare the tubes. Viscosity of the polymer solutions will, in turn, depend on factors such as the molecular weight of the polymer, polymer concentration, the solvent used to prepare the solutions, processing temperatures and shear rates.

Polymer solutions (approximately one percent to twenty percent (wt/wt) concentration), for example, prepared from PLGA with an intrinsic viscosity of 2 to 2.5 dl/g in dioxane comprising a drug in the range from about zero percent to about fifty percent may be directly deposited or casted on a mandrel using a needle, for example, at room temperature or at temperatures that will not degrade the drug, using a syringe pump. Alternately, mandrels may be dip coated in the solutions followed by drying and subsequent dip coating steps to obtain the required wall thickness. Different mandrel sizes may be used to obtain varying final tube dimensions, for example, diameter, wall thickness and the like. The polymer solutions may also contain radiopaque agents and other additives such as plasticizers, other polymers, and the like. The solvent from the drug loaded polymer tube on the mandrel may then be removed at temperatures and conditions that will not degrade the drug.

In order to prepare a hybrid stent comprised of metal and polymer, a thin metallic wire frame structure (e.g., same as the stent design) can be impregnated by the polymer solution during the solution-casting step or dipping coating step. This will allow the solution to completely encase the metallic wire frame and form a composite structure. This method will also provide good adhesion between metal and polymer during the tube drying process. Alternatively, the wire frame structure can be placed in the gel-like polymer tube after the solution casting or dip coating step. The wire frame structure can be of short lengths so that it can be distributed along the length of the tube at desired sites. Excimer laser, for example, can then cut the tube to form a hybrid or a composite stent. The wire frame will provide benefits such as low recoil, high stiffness and increased radiopacity. The wire frame can be made from different materials such as nitinol, stainless steel, alloys prepared from cobalt chromium or magnesium.

Different melt processes can also be used to combine metal with polymers to form the hybrid structure. For example, extrusion blow molding can be used in which polymers can be blow molded over and through the metal inserts. This creates one-piece polymer-metal hybrid structures with superior performance.

Another method can be a hybrid injection molding process. A thin wall metal frame is placed in the injection-molding tool. The tool closes and is then filled with a polymer resin as in a standard injection molding process. During the fill cycle, polymer flows through the openings and surrounds the edges of the metal frame profile. Solidification of the polymer creates a mechanical, interlocked connection between both materials producing a single unified component. Once cooled, the composite structure ejects from the tool as a hybrid product with no additional secondary operations. Alternatively, the polymer can be molded separately and can then be pressed with the metal frame in a secondary operation. These structures provide improved stiffness and strength in bending, compression, axial and torsional loading. Different additives can be added to the polymer to provide benefits such as conductivity, radiopacity, therapeutic effects, toughness, crystallinity, etc.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed:

1. A method of producing a substantially tubular intraluminal scaffold comprising:

providing a frame including: a plurality of hoop components configured as the primary radial load bearing elements of the intraluminal scaffold, the hoop components being formed as a continuous series of circumferentially oriented radial strut members and alternating radial arc members, wherein at least one of the plurality of hoop components comprises a non-bioabsorbable metallic material, and one or more connector elements interconnecting the plurality of hoop components, the connector elements comprising a continuous series of longitudinally oriented flexible strut members having substantially equal lengths and alternating flexible arc members forming a substantially N-shaped configuration, wherein the one or more connector elements are fabricated from a first bioabsorbable polymeric material;

extruding a second bioabsorbable polymeric material into a hollow tube inside the frame, the frame being contained inside a mold; and blowing air into the second bioabsorbable polymeric hollow tube inside the mold so that the second bioabsorbable polymeric material flows through openings of the frame and surrounds edges of the frame to form a one-piece polymer-metal hybrid structure with the non-bioabsorbable metallic material of the at least one of the plurality of hoop components of the frame and the second bioabsorbable polymeric material such that the bioabsorbable polymeric material forms a structural casing completely surrounding the frame and is configured to add structural integrity thereto, wherein a therapeutic agent is distributed throughout the second bioabsorbable polymeric material of the polymer-metal hybrid composite structure, the second bioabsorbable polymeric material of the polymer-metal hybrid composite structure being configured to hold a dose of the therapeutic agent.

2. A method of producing a substantially tubular intraluminal scaffold comprising:

providing a frame including: a plurality of hoop components configured as the primary radial load bearing elements of the intraluminal scaffold, the hoop components being formed as a continuous series of circumferentially oriented radial strut members and alternating radial arc members, wherein at least one of the plurality of hoop components comprises a non-bioabsorbable metallic material, and one or more connector elements interconnecting the plurality of hoop components, the connector elements comprising a continuous series of longitudinally oriented flexible strut members having substantially equal lengths and alternating flexible arc members forming a substantially N-shaped configuration, wherein the one or more connector elements are fabricated from a first bioabsorbable polymeric material and include a first therapeutic agent;

extruding a second bioabsorbable polymeric material into a hollow tube inside the frame, the frame being contained inside a mold; and blowing air into the second bioabsorbable polymeric hollow tube inside the mold so that the second bioabsorbable polymeric material flows through openings of the frame and surrounds edges of the frame to form a one-piece polymer-metal hybrid structure with the non-bioabsorbable metallic material of the at least one of the plurality of hoop components of the frame and the bioabsorbable polymeric material such that the second bioabsorbable polymeric material forms a structural casing completely surrounding the frame and is configured to add structural integrity thereto, wherein a second therapeutic agent is distributed throughout the second bioabsorbable polymeric material of the polymer-metal hybrid composite structure, the second bioabsorbable polymeric material of the polymer-metal hybrid composite structure being configured to hold a dose of the second therapeutic agent.

* * * * *